United States Patent [19]

Takaya et al.

[11] Patent Number: 4,596,829
[45] Date of Patent: * Jun. 24, 1986

[54] 7-ACYLAMINOCEPHALOSPORANIC ACID DERIVATIVES AND PROCESSES FOR THE PREPARATION THEREOF

[75] Inventors: Takao Takaya, Kawanishi; Hisashi Takasugi, Hamaguchinishi; Masayoshi Murata, Osaka; Akiteru Yoshioka, Kyoto, all of Japan

[73] Assignee: Fujisawa Pharmaceutical Co., Ltd., Osaka, Japan

[*] Notice: The portion of the term of this patent subsequent to Jun. 5, 2001 has been disclaimed.

[21] Appl. No.: 571,488

[22] Filed: Jan. 17, 1984

Related U.S. Application Data

[62] Division of Ser. No. 336,161, Dec. 31, 1981, Pat. No. 4,438,113.

[30] Foreign Application Priority Data

Dec. 31, 1980 [GB] United Kingdom ............... 8041635
Mar. 23, 1981 [GB] United Kingdom ............... 8108991
Sep. 1, 1981 [GB] United Kingdom ............... 8126500

[51] Int. Cl.[4] .................. C07D 501/20; A61K 31/545
[52] U.S. Cl. ..................................... 514/202; 544/22; 544/27; 544/28
[58] Field of Search ............................. 544/22, 27, 28; 424/246; 514/202

[56] References Cited

U.S. PATENT DOCUMENTS

| | | | |
|---|---|---|---|
| 4,008,246 | 2/1977 | Ochiai, II | 424/246 |
| 4,098,888 | 7/1978 | Ochiai et al. | 544/27 |
| 4,152,433 | 5/1979 | Kamiya | 544/22 |
| 4,254,119 | 3/1981 | Hamashima et al. | 544/22 |
| 4,293,550 | 10/1981 | Blumbach et al. | 544/28 |
| 4,396,618 | 8/1983 | Heymes et al. | 544/22 |
| 4,425,341 | 1/1984 | Takaya et al. | 544/22 |
| 4,452,851 | 6/1984 | Takaya | 544/22 |
| 4,460,583 | 7/1984 | Takaya | 544/22 |
| 4,462,999 | 7/1984 | Takaya | 544/27 |

Primary Examiner—Donald G. Daus
Assistant Examiner—Robert Benson
Attorney, Agent, or Firm—Oblon, Fisher, Spivak, McClelland & Maier

[57] ABSTRACT

This invention relates to novel 7-acylaminocephalosporanic acid derivatives and pharmaceutically acceptable salts thereof, of high antimicrobial activity, said novel derivatives having the formula

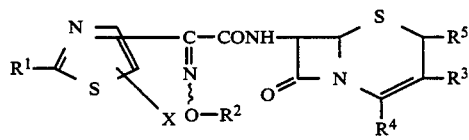

wherein
$R^1$ is amino or protected amino,
$R^2$ is carboxy(lower)alkyl, protected carboxy(lower)alkyl, carboxy(lower)alkenyl, protected carboxy(lower)alkenyl, or lower unsaturated aliphatic hydrocarbon,
$R^3$ is hydrogen, halogen, methyl, lower alkoxy, lower alkylthiomethyl, lower alkanoyloxymethyl or a heterocyclicthiomethyl which may have suitable substituents,
$R^4$ is carboxy or protected carboxy,
$R^5$ is hydrogen or lower alkyl, and
X is halogen, provided that when $R^3$ is lower alkanoyloxymethyl, then $R^2$ is lower unsaturated aliphatic hydrocarbon, and pharmaceutically acceptable salts thereof.

12 Claims, No Drawings

7-ACYLAMINOCEPHALOSPORANIC ACID DERIVATIVES AND PROCESSES FOR THE PREPARATION THEREOF

This is a division of application Ser. No. 336,161, filed Dec. 31, 1981 now U.S. Pat No. 4,438,113.

The present invention relates to novel 7-acylaminocephalosporanic acid derivatives and pharmaceutically acceptable salts thereof.

More particularly, it relates to novel 7-acylaminocephalosporanic acid derivatives and pharmaceutically acceptable salt thereof, which have antimicrobial activity, to processes for the preparation thereof, to a pharmaceutical composition comprising the same, and to a method of using the same therapeutically in the treatment of infectious diseases in human being and animals.

Accordingly, one object of the present invention, is to provide novel 7-acylaminocephalosporanic acid derivatives and pharmaceutically acceptable salts thereof, which are highly active against a number of pathogenic microorganisms and are useful as antimicrobial agents.

Another object of the present invention is to provide processes for the preparation of novel 7-acylaminocephalosporanic acid derivatives and salts thereof.

A further object of the present invention is to provide a pharmaceutical composition comprising, as active ingredients, said 7-acylaminocephalosporanic acid derivatives and pharmaceutically acceptable salts thereof.

Still further object of the present invention is to provide a method of using said 7-acylaminocephalosporanic acid derivatives and pharmaceutically acceptable salts thereof in the treatment of infectious diseases by pathogenic microorganisms in human being and animals.

The object 7-acylaminocephalosporanic acid derivatives are novel and can be represented by the following general formula:

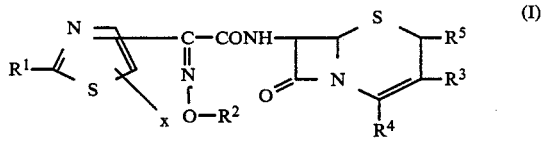

wherein
- $R^1$ is amino or protected amino,
- $R^2$ is carboxy(lower)alkyl, protected carboxy(lower)alkyl, carboxy(lower)alkenyl, protected carboxy(lower)alkenyl, or lower unsaturated aliphatic hydrocarbon,
- $R^3$ is hydrogen, halogen, methyl, lower alkoxy, lower alkylthiomethyl, lower alkanoyloxymethyl or a heterocyclicthiomethyl which may have suitable substituent(s),
- $R^4$ is carboxy or protected carboxy,
- $R^5$ is hydrogen or lower alkyl, and
- X is halogen, provided that when $R^3$ is lower alkanoyloxymethyl, then $R^2$ is lower unsaturated aliphatic hydrocarbon.

In the object compounds (I) and the corresponding starting compound (III) in Process 1 mentioned below, it is to be understood that there may be one or more stereoisomeric pair(s) such as optical and geometrical isomers due to asymmetric carbon atom and double bond in those molecules and such isomers are also included within the scope of the present invention.

With regard to geometrical isomers in the object compounds and the starting compounds, it is to be noted that, for example, the object compounds include syn isomer, anti isomer and a mixture thereof, and the syn isomer means one geometrical isomer having the partial structure represented by the following formula:

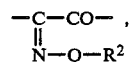

wherein $R^2$ is as defined above, and the anti isomer means the other geometrical isomer having the partial structure represented by the following formula:

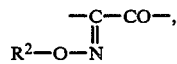

wherein $R^2$ is as defined above.

Regarding the other object and starting compound as mentioned above, the syn isomer and the anti isomer can also be referred to the same geometrical isomers as illustrated for the compounds (I).

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.); an intermolecular or intramolecular quaternary salt, and the like.

According to the present invention, the object compounds (I) and the pharmaceutically acceptable salts thereof can be prepared by the processes as illustrated by the following reaction schemes.

Process 1:

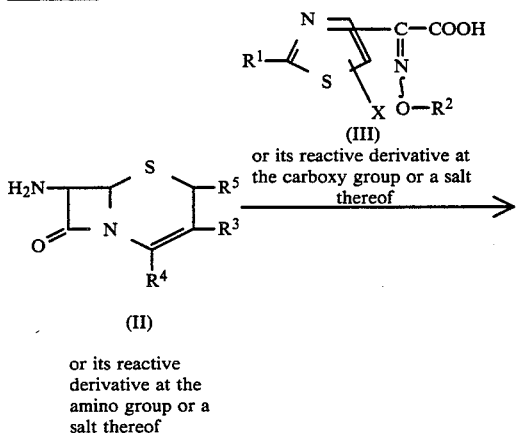

or its reactive derivative at the amino group or a salt thereof

-continued

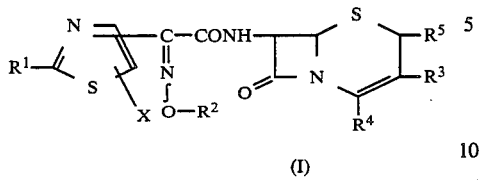

(I)

or a salt thereof

Process 2:

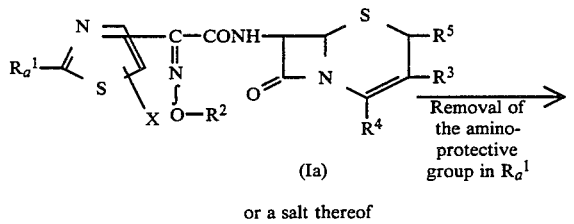

(Ia)  →  Removal of the amino-protective group in $R_a{}^1$ or a salt thereof

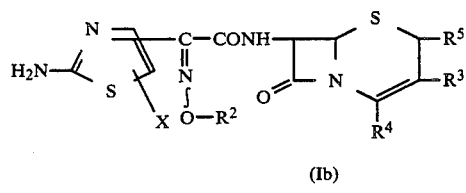

(Ib)

or a salt thereof

Process 3:

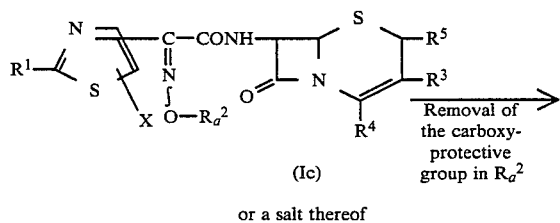

(Ic)  →  Removal of the carboxy-protective group in $R_a{}^2$ or a salt thereof

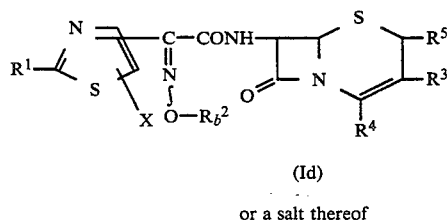

(Id)

or a salt thereof

Process 4:

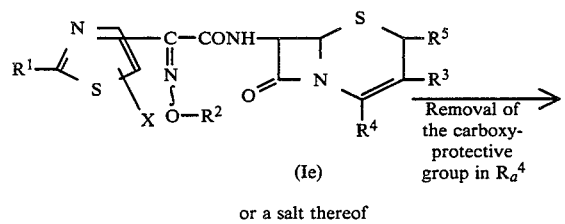

(Ie)  →  Removal of the carboxy-protective group in $R_a{}^4$ or a salt thereof

-continued

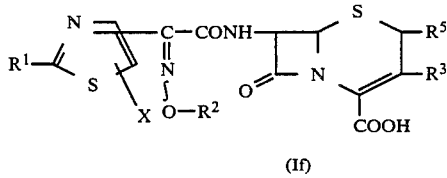

(If)

or a salt thereof in which
$R^1$, $R^2$, $R^3$, $R^4$, $R^5$ and X are each as defined above,
$R_a{}^1$ is protected amino,
$R_a{}^2$ is protected carboxy(lower)alkyl or protected carboxy(lower)alkenyl,
$R_b{}^2$ is carboxy(lower)alkyl or carboxy(lower)alkenyl, and
$R_a{}^4$ is protected carboxy.

Some of the starting compounds (III) are novel and can be prepared, for example, from the known compounds of the methods in the following processes.

Process (i):

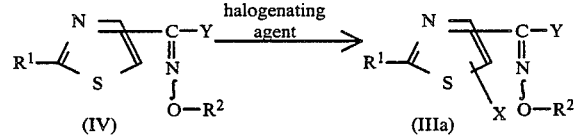

(IV)  →halogenating agent→  (IIIa)

or a salt thereof     or a salt thereof

Process (ii):

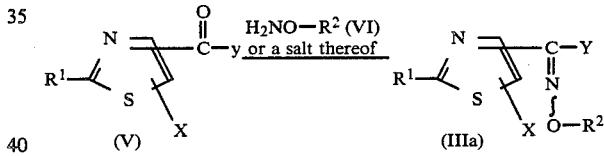

(V)  →$H_2NO-R^2$ (VI) or a salt thereof→  (IIIa)

or a salt thereof     or a salt thereof

Process (iii)

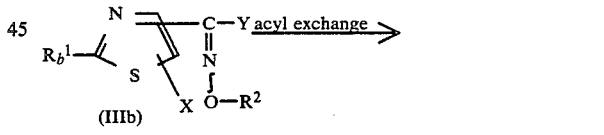

(IIIb)  →acyl exchange→ or a salt thereof

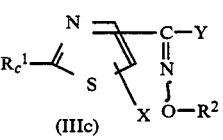

(IIIc)

or a salt thereof in which
$R^1$, $R^2$ and X are each as defined above,
Y is carboxy or protected carboxy,
$R_b{}^1$ is lower alkanoylamino, and
$R_c{}^1$ is trihalo(lower)alkanoylamino.

In the above and subsequent description of the present specification, suitable examples and illustration of the various definitions to be included within the scope thereof are explained in detail as follows.

The term "lower" in the present specification is intended to mean a group having 1 to 6 carbon atoms, unless otherwise indicated.

Suitable "lower alkyl" and "lower alkyl" moiety in the terms "carboxy(lower)alkyl", "protected carboxy(lower)alkyl" and "lower alkylthiomethyl" may include straight or branched one such as methyl, ethyl, propyl, isopropyl, butyl, isobutyl, pentyl, isopentyl, neopentyl, hexyl and the like, in which the preferred one is ($C_1$–$C_4$)alkyl.

Suitable "carboxy(lower)alkyl" may include carboxymethyl, 1-carboxyethyl, 2-carboxyethyl, 1-carboxypropyl, 2-carboxypropyl, 3-carboxypropyl, 1-carboxybutyl, 2-carboxybutyl, 3-carboxybutyl, 4-carboxybutyl, 5-carboxypentyl, 6-carboxyhexyl and the like, in which the preferred one is carboxy($C_1$–$C_4$)alkyl.

Suitable "lower alkenyl" moiety in the terms "carboxy(lower)alkenyl" and "protected carboxy(lower)alkenyl" may include straight or branched one such as vinyl, 1-propenyl, allyl, 1-(or 2 - or 3-)butenyl, 1-(or 2- or 3- or 4-)pentenyl, 1-(or 2- or 3- or 4- or 5-)hexenyl, 2-methyl-2-propenyl and the like, in which the preferred one is ($C_2$–$C_5$)alkenyl.

Suitable carboxy(lower)alkenyl may include 1-carboxyvinyl, 2-carboxyvinyl, 1-carboxy-1-propenyl, 2-carboxy-1-propenyl, 3-carboxy-1-propenyl, 1-carboxyallyl, 2-carboxyallyl, 3-carboxyallyl, 4-carboxy-1-(or 2 or 3-)butenyl, 5-carboxy-1-(or 2 or 3 or 4-)pentenyl, 6-carboxy-1-(or 2 or 3 or 4 or 5-)hexenyl, 3-carboxy-2-methyl-2-propenyl and the like, in which the preferred one is carboxy($C_2$–$C_5$)alkenyl.

Suitable "protected carboxy" and "protected carboxy" moiety in the terms "protected carboxy(lower)alkyl" and "protected carboxy(lower)alkenyl" may include an esterified carboxy and the like.

Suitable "esterified carboxy" may include lower alkyl ester (e.g. methyl ester, ethyl ester, propyl ester, isopropyl ester, butyl ester, isobutyl ester, t-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), mono(or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propionyloxyethyl ester, 1-acetoxypropyl ester, etc), lower alkanesulfonyl(lower)alkyl ester (e.g. mesylmethyl ester, 2-mesylethyl ester, etc.), ar(lower)alkyl ester which may have one or more substituent(s) such as mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, tert-butylphenyl ester, xylyl ester, mesityl ester, cumenyl ester, salicyl ester, etc.), heterocyclic ester (e.g. phthalidyl ester, etc.), and the like.

Suitable "lower unsaturated aliphatic hydrocarbon" may include lower alkenyl as exemplified above, cyclo(lower)alkyl (e.g. cyclopropenyl, cyclobutenyl, cyclopentenyl, cyclohexenyl, cycloheptenyl, etc.), in which the preferred one is ($C_5$–$C_6$)cycloalkenyl; lower alkynyl (e.g. propargyl, 2-(or 3-)butynyl, 2-(or 3- or 4-)pentynyl, 2-(or 3- or 4- or 5-)hexynyl, etc.), in which the preferred one is ($C_2$–$C_5$)alkynyl; and the like.

Suitable "protected amino" group may include an amino group substituted by a conventional amino-protective group which is used in penicillin and cephalosporin compounds, for example, acyl as mentioned below, ar(lower)alkyl such as mono-(or di or tri)phenyl(lower)alkyl (e.g. benzyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), etc.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$–$C_7$)-cycloalkanecarbonyl (e.g. (cyclohexanecarbonyl, etc.), amidino, and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclic-carbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include ar(lower)alkanoyl such as phenyl(lower)alkanoyl (e.g. phenylacetyl, phenylpropionyl, phenylhexanoyl, etc.), ar(lower)alkoxycarbonyl such as phenyl(lower) alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono-(or di or tri)halo(lower)alkanoyl (e.g. chloroacetyl, bromoacetyl, dichloroacetyl, trifluoroacetyl, etc.), mono-(or di or tri)halo(lower)alkoxycarbonyl (e.g. chloromethoxycarbonyl, dichloromethoxycarbonyl, 2,2,2-tri-chloroethoxycarbonyl, etc.) nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

Suitable "halogen" may include chlorine, iodine, bromine and fluorine.

Suitable "lower alkoxy" may include methoxy, ethoxy, propoxy, isopropoxy, butoxy, pentyloxy, hexyloxy and the like, and preferably methoxy.

Suitable "lower alkylthiomethyl" may include methylthiomethyl, ethylthiomethyl, propylthiomethyl, isobutylthiomethyl, pentylthiomethyl, hexylthiomethyl and the like, in which the preferred one is ($C_1$–$C_4$)alkylthiomethyl.

Suitable "lower alkanoyl" moiety in the term "lower alkanoyloxymethyl" may include formyl, acetyl, propionyl, butyryl, isobutyryl, valeryl, isovaleryl, pivaloyl, hexanoyl and the like, in which the preferred one is acetyl.

Suitable "heterocyclic group in the term "heterocyclicthiomethyl" which may have suitable substituent(s)" may include saturated or unsaturated, monocyclic or polycyclic heterocyclic group containing at least one hetero-atom such as an oxygen, sulfur, nitrogen atom, and the like. And, especially preferable heterocyclic group may be heterocyclic group such as unsaturated 3 to 8-membered (more preferably 5 to 6-membered) heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), triazinyl (e.g. 2,5-dihydro-1,2,4-triazinyl, 1,2,4-triazinyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2-oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.

saturated 3 to 8-membered (more preferable 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

Thus defined heterocyclic group may optionally have one to three suitable substituent(s) such as lower alkyl (e.g. methyl, ethyl, propyl, isopropyl, butyl, pentyl, hexyl, etc.), hydroxy, oxo, amino, halogen (e.g. chlorine, bromine, etc.), lower alkoxy (e.g. methoxy, ethoxy, propoxy, etc.), carboxy(lower)alkyl as exemplified above.

Preferable example of heterocyclic moieties having suitable substituent(s) may include thiadiazolyl having lower alkyl (e.g., methylthiadiazolyl, ethylthiadiazolyl, propylthiadiazolyl, etc.), tetrazolyl having lower alkyl (e.g., methyltetrazolyl, ethyltetrazolyl, propyltetrazolyl, etc.), tetrazolyl having carboxy(lower)alkyl [e.g., carboxymethyltetrazolyl(2-carboxyethyl)tetrazolyl, (3-carboxypropyl)tetrazolyl, etc.], thiazolyl having lower alkyl and carboxy(lower)alkyl such as 5-carboxy(lower)alkyl-4-lower alkylthiazolyl [e.g. 5-carboxymethyl-4-methylthiazolyl, 5-carboxymethyl-4-ethylthiazolyl, 5-carboxymethyl-4-propylthiazolyl, 5-carboxymethyl-4-isopropylthiazolyl, etc.] and 5-lower alkyl-4-carboxy(lower)alkylthiazolyl [e.g. 5-methyl-4-carboxymethylthiazolyl, 5-ethyl-4-carboxymethylthiazolyl, 5-propyl-4-carboxymethylthiazolyl, 5-isopropyl-4-carboxyethylthiazolyl, etc.] and the like. etc.] and the like.

Suitable "lower alkanoyl" moiety in the terms "lower alkanoylamino" and "trihalo(lower)alkanoylamino" may include the ones as exemplified above, in which the preferred one is formyl and acetyl.

The processes 1 to 4 for the preparation of the object compounds (I) of the present invention are explained in detail in the following.

Process 1

The compound (I) or a salt thereof can be prepared by reacting the compound (II) or its reactive derivative at the amino group or a salt thereof with the compound (III) or its reactive derivative at the carboxy group or a salt thereof.

Suitable salt of the starting compound (II) and (III) may include the same ones as illustrated for the compounds (I).

Suitable reactive derivative at the amino group of the compound (II) may include a conventional one, for example, a silyl derivative formed by the reaction of the compound (II) with a silyl compound such as bis(trimethylsilyl)acetamide, trimethylsilylacetamide, etc.; isocyanate; isothiocyanate; Schiff's base or its tautomeric enamine type isomer formed by the reaction of the amino group with a carbonyl compound such as an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g. acetone, methyl ethyl ketone, methyl isobutyl ketone, acetylacetone, ethyl acetoacetate, etc.), and the like.

Suitable reactive derivative of the compound (III) may include, for example, an acid halide, an acid anhydride, an activated amide, an activated ester, and the like, and preferably an acid chloride and acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with a heterocyclic compound containing imino function such as imidazole, 4-substituted imidazole, dimethylpyrazole, triazole or tetrazole; an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivative can optionally be selected from the above according to the kinds of the compounds (II) and (III) to be used practically.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compound (e.g. pyridine, lutidine, picoline, etc.), quinoline, and the like.

In case that the compound (III) is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as N,N-di(lower)alkylformamide (e.g. N,N-dimethylformamide, etc.), N-methylformamide or the like with a halogen compound such as thionyl chloride, phosphoryl chloride, phosgene or the like.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

Among these solvents, hydrophilic solvents may be used in a mixture with water.

The reaction temperature is not critical and the reaction is usually carried out under cooling to warming.

Process 2

The compound (Ib) or a salt thereof can be prepared by subjecting the compound (Ia) or a salt thereof to removal reaction of the amino-protective group in $R_a^1$.

Suitable method for this removal reaction may include conventional one such as hydrolysis, reduction, and the like.

(i) For hydrolysis:

Hydrolysis is preferably carried out in the presence of an acid or a base.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, methanesulfonic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

Suitable base may be the same organic and inorganic bases as those in Process 1.

The acid or base suitable for this hydrolysis can be selected according to the kinds of the protective group to be removed, for example, this hydrolysis can preferably be applied to the amino-protective group for $R_a^1$ such as substituted or unsubstituted lower alkoxycarbonyl, substituted or unsubstituted lower alkanoyl.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to at somewhat elevated temperature.

(ii) For Reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction manner can be selected according to the kinds of the protective group to be removed, for example, the chemical reduction can preferably be applied to the amino-protective group for $R_a{}^1$ such as halo(lower)alkoxycarbonyl and the like, and catalytic reduction can preferably be applied to that such as substituted or unsubstituted ar(lower)alkoxycarbonyl, and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually carried out under cooling to warming.

The methods thus explained may be selected depending upon the kind of the protective groups to be removed.

The present invention includes, within the scope of the invention cases that the protected carboxy group(s) in $R^2$ and $R^4$ are transformed into the corresponding free carboxy group(s), respectively during the reaction.

Process 3

The compound (Id) or a salt thereof can be prepared by subjecting the compound (Ic) or a salt thereof to removal reaction of the carboxy-protective group in $R_a{}^2$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group of the compound (Ia) in Process 2, and therefore are to be referred to said explanation.

The present invention includes, within the scope of the invention, cases that the protected amino group in $R^1$ and/or the protected carboxy group in $R^4$ are transformed into a free amino group and/or a free carboxy group, respectively during the reaction.

Process 4

The compound (If) or a salt thereof can be prepared by subjecting the compound (Ie) or a salt thereof to removal reaction of the carboxy-protective group in $R_a{}^4$.

This reaction is carried out substantially in the same manner as explained in Process 3.

The present invention includes, within the scope of the invention, the cases that the protected amino group in $R^1$ and/or the protected carboxy group in $R^2$ are transformed into a free amino group and/or a free carboxy group, respectively, during the reaction.

The object compounds (I) obtained according to the Processes 1 to 4 as explained above can be isolated and purified in a conventional manner, for example, extraction, precipitation, fractional crystallization, recrystallization, chromatography, and the like.

Processes (i), (ii) and (iii) for the preparation of the starting compound (III) are explained in detail in the following.

Process (i)

The compound (IIIa) or a salt thereof can be prepared by reacting the compound (IV) or a salt thereof with a halogenating agent.

Suitable salt of the compound (IIIa) and (IV) may include the same salt as exemplified for the compounds (I).

Suitable halogenating agent used in this reaction may include one which can be applied to conversion of a hydrogen to a halogen such as halogen (e.g. chlorine, bromine, etc.), trihalogenoisocyanuric acid (e.g. trichloroisocyanuric acid, etc.), sodium salt of N-chloro-4-methylbenzenesulfonamide, N-halogenoamide (e.g. N-chloroacetamide, N-bromoacetamide, etc.), N-halogenoimide (e.g. N-chlorosuccinimide, N-bromosuccinimide, N-chlorophthalimide, N-bromophthalimide, etc.), alkyl hypochlorite (e.g. tert-butyl hypochlorite, etc.), and the like.

This reaction is usually carried out in a conventional solvent which does not adversely influence the reaction such as methanol, ethanol, isopropylalcohol methylene chloride, chloroform, ethylene chloride, tetrahydrofuran, dioxane, N,N-dimethylformamide, water, formic acid, acetic acid, etc., or a mixture thereof.

The reaction temperature is not critical and the reaction is usually carried out under cooling to warming.

Process (ii)

The compound (IIIa) or a salt thereof can be prepared by reacting the compound (V) or a salt thereof with the compound (VI) or a salt thereof.

Suitable salts of the compound (VI) may include the same acid addition salts as exemplified for the compounds (I).

In this reaction, when the compound (VI) is used in a salt form, this reaction can also be carried out in the presence of a base as exemplified in Process 1.

This reaction is usually carried out in a conventional solvent which does not adversely influence the reaction such as water, methanol, ethanol, propanol, dioxane, tetrahydrofuran, etc., or a mixture thereof.

The reaction temperature is not critical and the reaction is usually carried out under cooling to warming.

Process (iii)

The compound (IIIc) or a salt thereof can be prepared by subjecting the compound (IIIb) or a salt thereof to the acyl exchange reaction.

The present acyl exchange reaction can be carried out by reacting the compound (IIIb) or a salt thereof with an acylating agent. Suitable acylating agent may include R⁶-OH (VII) [wherein R⁶ is trihalo(lower)alkanoyl] or its reactive derivatives or a salt thereof.

Suitable reactive derivatives can be referred to the ones as mentioned in Process 1. The present acyl exchange reaction can be carried out in a similar manner to that of aforementioned Process 1.

The starting compounds thus prepared can be isolated in a conventional manner as mentioned for the object compounds of the present invention.

It is to be noted that, in the aforementioned reactions in Processes 1 to 4 and (i) to (iii) or the post-treatment of the reaction mixture therein, in case that the starting or object compounds possess an optical and/or geometrical isomer(s), it may occasionally be transformed into the other optical and/or geometrical isomer(s), and such cases are also included within the scope of the present invention.

In case that the object compounds (I) have a free carboxy group or free amino group at the 4th or 7th position thereof, it may be transformed into its pharmaceutically acceptable salts by a conventional method.

The object compounds (I) and the pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents, especially for oral administration as shown in the following data.

Now in order to show the utility of the object compounds (I), the test data on the antimicrobial activity of some representative compounds (I) of this invention are shown in the following.

(1) Test 1: in Vitro Antimicrobial Activities.

Test Compounds

No. 1: 7-[2-(2-amino-5-chlorothiazol-4-yl)-2-(1-carboxyethoxyimino)acetamido]-3-cephem-4-carboxylic acid (syn isomer).

No. 2: 7-[2-(2-amino-5-chlorothiazol-4-yl)-2-propargyloxyiminoacetamido]-3-(1,3,4-thiadiazol-2-yl)thiomethyl-3-cephem-4-carboxylic acid (syn isomer).

No. 3: 7-[2-(2-amino-5-chlorothiazol-4-yl)-2-carboxymethoxyiminoacetamido]-3-(1,3,4-thiadiazol-2-yl)thiomethyl-3-cephem-4-carboxylic acid (syn isomer).

No. 4: 7-[2-(2-amino-5-chlorothiazol-4-yl)-2-allyloxyiminoacetamido]-3-(1,3,4-thiadiazol-2-yl)thiomethyl-3-cephem-4-carboxylic acid (syn isomer).

No. 5: 7-[2-(2-amino-5-chlorothiazol-4-yl)-2-(2-cyclopenten-1-yl)oxyiminoacetamido]-3-(1,3,4-thiadiazol-2-yl)thiomethyl-3-cephem-4-carboxylic acid (syn isomer).

No. 6: 7-[2-(2-amino-5-chlorothiazol-4-yl)-2-carboxymethoxyiminoacetamido]-3-chloro-3-cephem-4-carboxylic acid (syn isomer).

Test Method

In vitro antimicrobial activity was determined by the two-fold agar-plate dilution method as described below.

One loopful of an overnight culture of each test strain in Tripticase-soy broth (approximately 10⁸ viable cells per ml) was streaked on heart infusion agar (HI-agar) containing graded concentrations of antimicrobial agents, and the minimal inhibitory concentration (MIC) was expressed in term of μg/ml after incubation at 37° C. for 20 hours.

Test Results 1
MIC (μg/ml)

| Strains | Compounds | | | | | |
|---|---|---|---|---|---|---|
| | 1 | 2 | 3 | 4 | 5 | 6 |
| *Proteus vulgaris* IAM-1025 | 0.05 | 1.56 | 0.025 | 1.56 | 0.39 | 0.05 |
| *Pseudomonas aeruginosa* NCTC-10490 | 0.78 | 0.78 | 0.78 | 0.78 | 0.39 | 0.78 |

For therapeutic administration, the object compounds (I) and the pharmaceutically acceptable salts thereof of the present invention are used in the form of conventional pharmaceutical preparation which contains said compound, as active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like. If needed, there may be included in the above preparations auxiliary substances, stabilizing agents, wetting agents and other commonly used additives such as as lactose, magnesium stearate, terra alba, sucrose, corn starch, talc, stearic acid, gelatin, agar, pectin, peanut oil, olive oil, cacao butter, ethylene glycol and the like.

While the dosage of the compounds (I) may vary from and also depend upon the age, conditions of the patient, a kind of diseases, a kind of the compounds (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds (I) of the present invention may be used in treating diseases infected by pathogenic microorganisms.

The following preparations and examples are given for the purpose of illustrating the present invention.

Preparation of the starting compounds

Preparation 1

A solution of chlorine (3.2 g) in acetic acid (44 ml) was dropwise added to a solution of 2-(2-formamidothiazol-4-yl)-2-(propargyloxyimino)acetic acid (syn isomer) (10 g) in chloroform (250 ml) at 0° C., and the mixture was stirred for 30 minutes at same temperature. The resultant solution was added to a saturated aqueous solution of sodium bicarbonate and adjusted to pH 7.5 with 10% aqueous solution of sodium hydroxide. The separated aqueous layer was adjusted to pH 2.0 with conc. hydrochloric acid and extracted with ethyl acetate. The extract was washed with a saturated aqueous solution of sodium chloride, dried over magnesium sulfate and evaporated in vacuo. The residue was washed with diisopropyl ether and collected by filtration to give 2-(2-formamido-5-chlorothiazol-4-yl)-2-propargyloxyiminoacetic acid (syn isomer) (5.96 g), mp 161° to 162° C. (dec.).

IR (Nujol): 3280, 3120, 2120, 1730, 1690, 1650 cm⁻¹.

NMR (DMSO-d₆, δ): 3.53 (1H, m), 4.86 (2H, d, J=2.0 Hz), 8.58 (1H, s), 12.97 (1H, broad s).

Preparation 2

The following compounds were obtained according to a similar manner to that of Preparation 1.

(1) 2-(2-Formamido-5-chlorothiazol-4-yl)-2-tertbutoxycarbonylmethoxyiminoacetic acid (syn isomer), mp 166° to 167° C. (dec.).

IR (Nujol): 3150, 1725, 1690, 1650, 1560, 1530 cm$^{-1}$.

NMR (DMSO-d$_6$, δ): 1.47 (9H, s), 4.75 (2H, s), 8.7 (1H, s), 12.8 (1H, s).

(2) 2-(2-Formamido-5-chlorothiazol-4-yl)-2-(1-tert-butoxycarbonylethoxyimino)acetic acid (syn isomer).

NMR (DMSO-d$_6$, δ): 1.26–1.64 (12H, m), 4.69 (1H, q, J=7.0 Hz), 8.55 (1H, s).

(3) 2-[2-(2,2,2-Trifluoroacetamido)-5-chlorothiazol-4-yl]-2-propargyloxyiminoacetic acid (syn isomer), mp. 178° to 180° C.

IR (Nujol): 3300, 2140, 1725, 1600 cm$^{-1}$.

(4) 2-(2-Formamido-5-chlorothiazol-4-yl)-2-allyloxyiminoacetic acid (syn isomer), mp. 166° to 167° C.

IR (Nujol): 3140, 1730, 1695, 1650 cm$^{-1}$.

(5) 2-(2-Formamido-5-chlorothiazol-4-yl)-2-(2-cyclopenten-1-yl)oxyiminoacetic acid (syn isomer), mp. 148° to 150° C.

IR (Nujol): 3150, 1725, 1700, 1655, 1540 cm$^{-1}$.

(6) 2-Allyloxyimino-2-(5-chloro-2-trifluoroacetamidothiazol-4-yl)acetic acid (syn isomer), mp. 162° C. (dec.).

IR (Nujol): 1720 cm$^{-1}$.

(7) 2-(5-Chloro-2-trifluoroacetamidothiazol-4-yl)2-t-butoxycarbonylmethoxyiminoacetic acid (syn isomer), mp. 145° to 146° C.

IR (Nujol): 3180, 1740, 1721, 1595 cm$^{-1}$.

(8) 2-(5-Chloro-2-formamidothiazol-4-yl)-2-(3-t-butoxycarbonyl-2-propenyloxyimino)acetic acid (syn isomer), mp. 139° to 142° C. (dec.).

IR (Nujol): 3150, 1705, 1655 cm$^{-1}$.

Preparation 3

Ethyl (2-formamido-5-chlorothiazol-4-yl)glyoxylate (14.5 g) was added to a solution of 1N aqueous potassium hydroxide (110 ml) at ambient temperature, and the mixture was stirred for 10 minutes to prepare the solution of potassium (2-formamido-5-chlorothiazol-4-yl)glyoxylate. After this solution was adjusted to pH 2 with 10% hydrochloric acid under ice-cooling, thereto were added pyridine (20 ml) and a solution of tert-butyl 2-aminooxyacetate (10.3 g) in tetrahydrofuran (50 ml), followed by stirring at ambient temperature for 5 hours. After the reaction mixture was washed with ethyl acetate, the remaining aqueous solution was adjusted to pH 1.5 with 10% hydrochloric acid and extracted with ethyl acetate. The extract was washed with an aqueous sodium chloride and then dried over magnesium sulfate. Removal of the solvent gave 2-(2-formamido-5-chlorothiazol-4-yl)-2-tertbutoxycarbonylmethoxyiminoacetic acid (syn isomer) (8.5 g), mp 166° to 167° C. (dec.).

IR (Nujol): 3150, 1725, 1690, 1650, 1560, 1530 cm$^{-1}$.

NMR (DMSO-d$_6$, δ): 1.47 (9H, s), 4.75 (2H, s), 8.7 (1H, s), 12.8 (1H, s).

Preparation 4

Ethyl (2-formamido-5-chlorothiazol-4-yl)glyoxylate (10.0 g) was added to the 1N aqueous solution of potassium hydroxide (76.1 ml) at ambient temperature and stirred for 10 minutes. The reaction mixture was adjusted to pH 2.0 with 10% aqueous hydrochloric acid under ice cooling. A solution of 1-tert-butoxycarbonylethoxyamine (8.4 g) in tetrahydrofuran (35 ml) was added to the stirred suspension of the above mixture in pyridine (13.9 ml) at ambient temperature and stirred for 4 hours at same temperature. The resulting mixture was adjusted to pH 7.5 with a saturated aqueous solution of sodium bicarbonate, and washed with ethyl acetate. The separated aqueous layer was adjusted to pH 2.0 with 10% aqueous hydrochloric acid and extracted with ethyl acetate. The extracts were washed with a saturated aqueous solution of sodium chloride, dried over magnesium sulfate and evaporated in vacuo. The residue was washed with diisopropyl ether and collected by filtration to give 2-(2-formamido-5-chlorothiazol-4-yl)-2-(1-tert-butoxycarbonylethoxyimino)acetic acid (syn isomer) (2.31 g).

NMR (DMSO-d$_6$, δ): 1.26–1.64 (12H, m), 4.69 (1H, q, J=7.0 Hz), 8.55 (1H, s).

Preparation 5

Ethyl (2-formamido-5-chlorothiazol-4-yl)glyoxylate (40.0 g) was added to 1N aqueous solution of potassium hydroxide (305 ml) at ambient temperature and stirred for 10 minutes. The reaction mixture was adjusted to pH 2.0 with 10% aqueous hydrochloric acid under ice cooling. A solution of allyloxyamine (14.4 g) in tetrahydrofuran (200 ml) was added to the stirred suspension of the above mixture in pyridine (54.1 g) at ambient temperature and stirred for 4 hours at the same temperature. The resultant mixture was adjusted to pH 7.5 with a saturated aqueous solution of sodium bicarbonate, and washed with ethyl acetate. The separated aqueous layer was adjusted to pH 2.0 with 10% hydrochloric acid and extracted with ethyl acetate. The extract was washed with a saturated aqueous solution of sodium chloride, dried over magnesium sulfate and evaporated under reduced pressure. The residue was washed with diisopropyl ether and collected by filtration to give 2-(2-formamido-5-chlorothiazol-4-yl)-2-allyloxyiminoacetic acid (syn isomer, 24.74 g), mp. 166° to 167° C.

IR (Nujol): 3140, 1730, 1695, 1650 cm$^{-1}$.

NMR (DMSO-d$_6$, δ): 4.69 (2H, m), 5.09–5.59 (2H, m), 5.67–6.41 (1H, m), 8.52 (1H, s), 12.87 (1H, broad).

Preparation 6

The following compounds were prepared according to the similar manners to those of Preparations 3 to 5.

(1) 2-(2-Formamido-5-chlorothiazol-4-yl)-2-(2-cyclopenten-1-yl)oxyiminoacetic acid (syn isomer), mp. 148° to 150° C.

IR (Nujol): 3150, 1725, 1700, 1655, 1540 cm$^{-1}$.

NMR (DMSO-d$_6$, δ): 1.65–2.5 (4H, m), 5.35 (1H, m), 5.90 (1H, m), 6.10 (1H, m), 8.53 (1H, s), 12.9 (1H, s).

(2) 2-(2-Formamido-5-chlorothiazol-4-yl)-2-propargyloxyiminoacetic acid (syn isomer), mp. 161° to 162° C. (dec.).

IR (Nujol): 3280, 3120, 2120, 1730, 1690, 1650 cm$^{-1}$.

NMR (DMSO-d$_6$, δ): 3.53 (1H, m), 4.86 (2H, d, J=2.0 Hz), 8.58 (1H, s), 12.97 (1H, broad s).

(3) 2-[2-(2,2,2-Trifluoroacetamido)-5-chlorothiazol-4-yl]-2-propargyloxyiminoacetic acid (syn isomer). mp. 178° to 180° C.

IR (Nujol): 3300, 2140, 1725, 1600 cm$^{-1}$.

(4) 2-Allyloxyimino-2-(5-chloro-2-trifluoroacetamidothiazol-4-yl)acetic acid (syn isomer), mp. 162° C. (dec.).

IR (Nujol): 1720 cm$^{-1}$.

(5) 2-(5-Chloro-2-trifluoroacetamidothiazol-4-yl)-2-t-butoxycarbonylmethoxyiminoacetic acid (syn isomer), mp. 145° to 146° C.

IR (Nujol): 3180, 1740, 1721, 1595 cm$^{-1}$.

(6) 2-(5-Chloro-2-formamidothiazol-4-yl)-2-(3-t-butoxycarbonyl-2-propenyloxyimino)acetic acid (syn isomer), mp. 139° to 142° C. (dec.).

IR (Nujol): 3150, 1705, 1655 cm$^{-1}$.

NMR (DMSO-d$_6$, δ): 1.45 (9H, s), 4.90 (2H, d, J=4.0 Hz), 5.93 (1H, d, J=16.0 Hz), 6.88 (1H, d-t, J=16.0 Hz, 4.0 Hz), 8.55 (1H, s), 12.87 (1H, broad s).

Preparation 7

2,2,2-Trifluoroacetic anhydride (12.8 g) was added to the stirred suspension of 2-(2-formamido-5-chlorothiazol-4-yl)-2-propargyloxyiminoacetic acid (syn isomer, 8.0 g) in tetrahydrofuran (40.0 ml) at −10° to −5° C. Triethylamine (6.2 g) was added to the reaction mixture at −10° to −2° C., and stirred for 2 hours at 0° to 5° C. The reaction mixture was poured into a mixture of ethyl acetate and water, and adjusted to pH 7.5 with 10% aqueous solution of sodium hydroxide. The separated aqueous layer was adjusted to pH 2.5 with 10% hydrochloric acid and extracted with ethyl acetate. The ethyl acetate layer was washed with a saturated aqueous solution of sodium chloride, dried over magnesium sulfate and evaporated under reduced pressure. The residue was washed with di-isopropyl ether and collected by filtration to give 2-[2-(2,2,2-trifluoroacetamido)-5-chlorothiazol-4-yl]-2-propargyloxyiminoacetic acid (syn isomer, 5.9 g), mp. 178° to 180° C.

IR (Nujol): 3300, 2140, 1725, 1600 cm$^{-1}$.

NMR (DMSO-d$_6$, δ): 3.53 (1H, m), 4.88 (2H, d, J=2.0 Hz), 12.25 (1H, broad s).

Preparation 8

The following compounds were prepared according to a similar manner to that of Preparation 7.

(1) 2-Allyloxyimino-2-(5-chloro-2-trifluoroacetamidothiazol-4-yl)acetic acid (syn isomer), mp. 162° C. (dec.).

IR (Nujol): 1720 cm$^{-1}$.

NMR (DMSO-d$_6$, δ): 4.72 (2H, d, J=6.0 Hz), 5.11–5.61 (2H, m), 5.73–6.43 (1H, m).

(2) 2-(5-Chloro-2-trifluoroacetamidothiazol-4-yl)-2-t-butoxycarbonylmethoxyiminoacetic acid (syn isomer), mp. 145° to 146° C.

IR (Nujol): 3180, 1740, 1721, 1595 cm$^{-1}$.

NMR (DMSO-d$_6$, δ): 1.43 (9H, s), 4.67 (2H, s), 11.6 (1H, broad s).

EXAMPLE 1

Vilsmeier reagent was prepared from phosphorus oxychloride (1.4 g) and dimethyl formamide (0.67 g) in ethyl acetate (2.68 ml) in usual manner. 2-(5-Chloro-2-formamidothiazol-4-yl)-2-t-butoxycarbonylmethoxyiminoacetic acid (syn isomer) (2.8 g) was added to the stirred suspension of Vilsmeier reagent in tetrahydrofuran (30 ml) under ice cooling and stirred for 20 minutes at same temperature to produce an activated solution. N-(trimethylsilyl)acetamide (6.4 g) was added to the stirred suspension of 7-amino-3-methyl-3-cephem-4-carboxylic acid (1.5 g) in tetrahydrofuran (30 ml), and stirred for 20 minutes at 35° C. to 40° C. To the solution was added the above activated solution at −10° C. and stirred at same temperature for 30 minutes. Water and ethyl acetate were added to the reaction mixture and the separated organic layer was added to water and the mixture was adjusted to pH 7.5 with saturated aqueous sodium bicarbonate. The separated aqueous layer was adjusted to pH 2.0 with 10% aqueous hydrochloric acid and extracted with ethyl acetate. The extract layer was washed with saturated aqueous sodium chloride, dried over magnesium sulfate and evaporated to give 7-[2-(5-chloro-2-formamidothiazol-4-yl)-2-t-butoxycarbonylmethoxyiminoacetamido]-3-methyl-3-cephem-4-carboxylic acid (syn isomer) (3.03 g).

IR (Nujol): 3170, 1775, 1720 cm$^{-1}$.

NMR (DMSO-d$_6$, δ): 1.47 (9H, s), 2.45 (3H, s), 3.48 (2H, q, J=19.0 Hz), 4.65 (2H, s), 5.13 (1H, d, J=4.0 Hz), 5.80 (1H, d-d, J=4.0 Hz 8.0 Hz), 8.56 (1H, s), 9.52 (1H, d, J=8.0 Hz), 12.86 (1H, broad s).

EXAMPLE 2

Vilsmeier reagent was prepared from phosphorus oxychloride (2.0 g) and dimethylformamide (0.95 g) in ethyl acetate (3.8 ml) in usual manner. 2-(5-chloro-2-formamidothiazol-4-yl)-2-t-butoxycarbonylmethoxyiminoacetic acid (syn isomer) (4.0 g) was added to the stirred suspension of Vilsmeier reagent in tetrahydrofuran (50 ml) under ice cooling and stirred for 20 minutes at same temperature to produce an activated solution. N-(trimethylsilyl)acetamide (9.2 g) was added to the stirred suspension of p-nitrobenzyl-7-amino-3-chloro-3-cephem-4-carboxylate hydrochloride (4.1 g) in tetrahydrofuran (80 ml) and stirred for 20 minutes at 35° C. to 40° C. To the solution was added the above activated solution at −10° C. and stirred at same temperature for 30 minutes. Water and ethyl acetate were added to the reaction mixture. The separated organic layer was washed with saturated aqueous sodium bicarbonate, aqueous sodium chloride and dried over magnesium sulfate. The solvent was evapolated to give p-nitrobenzyl 7-[2-(5-chloro-2-formamidothiazol-4-yl)-2-t-butoxycarbonylmethoxyiminoacetamido]-3-chloro-3-cephem-4-carboxylate (syn isomer) (6.3 g).

IR (Nujol): 1780, 1720, 1675, 1600 cm$^{-1}$.

NMR (DMSO-d$_6$, δ): 1.43 (9H, s), 3.91 (2H, q, J=18.0 Hz), 4.62 (2H, s), 5.31 (1H, d, J=5.0 Hz), 5.45 (2H, s), 5.94 (1H, d-d, J=5.0 Hz 8.0 Hz), 7.68 (2H, d, J=8.0 Hz), 8.23 (2H, d, J=8.0 Hz), 8.51 (1H, s), 9.67 (1H, d, J=8.0 Hz), 12.82 (1H, broad s).

EXAMPLE 3

Vilsmeier reagent was prepared from phosphorus oxychloride (1.2 g) and N,N-dimethylformamide (0.6 g) in ethyl acetate (2.4 ml) in a usual manner. 2-(2-Formamido-5-chlorothiazol-4-yl)-2-tert-butoxycarbonylmethoxyiminoacetic acid (syn isomer) (2.4 g) was added to the stirred suspension of Vilsmeier reagent in dry tetrahydrofuran (24 ml) under ice-cooling and stirred for 20 minutes at same temperature [Solution A]. N-Trimethylsilylacetamide (6.4 g) was added to the stirred suspension of 7-amino-3-(1,3,4-thiadiazol-2-yl)thiomethyl-3-cephem-4-carboxylic acid (2.0 g) in tetrahydrofuran (40 ml), and the mixture was stirred for 30 minutes at 35° to 40° C. To the solution was added the solution [Solution A] at −10° C., and the resulting solution was stirred at same temperature for 30 minutes. Water and ethyl acetate were added to the reaction mixture at −10° C. The organic layer was separated and added to water. The mixture was adjusted to pH 7.5 with a saturated aqueous solution of sodium bicarbonate. The aqueous layer was separated and adjusted to pH 2.0 with 10% aqueous hydrochloric acid, and then extracted with ethyl acetate. The extract was washed with a saturated aqueous solution of sodium chloride, dried over magnesium sulfate and evaporated in vacuo to give 7-[2-(2-formamido-5-chlorothiazol-4-yl)-2-tertbutoxycarbonylmethoxyiminoacetamido]-3-(1,3,4,-thiadiazol-2-yl)thiomethyl-3-cephem-4-carboxylic acid (syn isomer) (3.72 g).

IR (Nujol): 1775, 1710, 1670 cm$^{-1}$.

NMR (DMSO-d$_6$, δ): 1.44 (9H, s), 3.71 (2H, m), 4.45 (2H, q, J=14.0 Hz), 4.64 (2H, s), 5.17 (1H, d, J=5.0 Hz), 5.87 (1H, dd, J=5.0 Hz, 8.0 Hz), 8.56 (1H, s), 9.56 (1H, s), 9.60 (1H, d, J=8.0 Hz), 12.90 (1H, s).

EXAMPLE 4

Vilsmeier reagent prepared from N,N-dimethylformamide (0.46 ml) and phosphorous oxychloride (0.55 ml) was suspended in dry tetrahydrofuran (20 ml). To the suspension was added 2-(2-formamido-5-chlorothiazol-4-yl)-2-tert-butoxycarbonylmethoxyiminoacetic acid (syn isomer) (1.8 g) under ice-cooling with stirring and then the solution was stirred at the same temperature for an hour to prepare the activated acid solution. To the solution of 7-amino-3-cephem-4-carboxylic acid (1.1 g) and N-trimethylsilylacetamide (6.5 g) in methylene chloride (20 ml) was added the activated acid solution obtained above all at once at −20° C., and the solution was stirred at −20° C. to −10° C. for an hour. After water and ethyl acetate were added to the resultant solution, the mixed solution was adjusted to pH 7.3 with a saturated aqueous solution of sodium bicarbonate. Then the aqueous layer was adjusted to pH 2.0 with conc. hydrochloric acid, extracted with mixed solvent of ethyl acetate (100 ml) and tetrahydrofuran (50 ml). The organic layer was washed with a saturated aqueous solution of sodium chloride and dried over magnesium sulfate. After removing the solvent, diisopropyl ether was added to the residue. The insoluble residue was collected by filtration to give 7-[2-(2-formamido-5-chlorothiazol-4-yl)-2-tert-butoxycarbonylmethoxyiminoacetamido]-3-cephem-4-carboxylic acid (syn isomer) (2.35 g), mp 145° to 149° C. (dec.).

IR (Nujol): 3200, 1775, 1720, 1670 cm$^{-1}$.

NMR (DMSO-d$_6$, δ): 1.45 (9H, s), 3.60 (2H, m), 4.60 (2H, s), 5.09 (1H, d, J=5 Hz), 5.87 (1H, dd, J=5 Hz, 8 Hz), 6.47 (1H, m), 8.50 (1H, s), 9.50 (1H, d, J=8 Hz).

EXAMPLE 5

Vilsmeier reagent was prepared from phosphorus oxychloride (1.1 g) and N,N-dimethylformamide (0.5 g) in ethyl acetate (2.0 ml) in a conventional manner. 2-[2-(2,2,2-Trifluoroacetamido)-5-chlorothiazol-4-yl]-2-propargyloxyiminoacetic acid (syn isomer, 2.2 g) was added to the stirred suspension of Vilsmeier reagent in tetrahydrofuran (22 ml) under ice cooling and stirred for 20 minutes at same temperature [Solution A]. Trimethylsilylacetamide (5.1 g) was added to the stirred suspension of 7-aminocephalosporanic acid (1.5 g) in tetrahydrofuran (30 ml); and the mixture was stirred for 30 minutes at 35° to 40° C. To the solution was added the solution [Solution A] at −10° C., and the resulting solution was stirred at the same temperature for 30 minutes. Water and ethyl acetate were added to the reaction mixture at −10° C. The organic layer was separated and added to water. The mixture was adjusted to pH 7.5 with a saturated aqueous solution of sodium bicarbonate. The aqueous layer was separated and adjusted to pH 2.0 with 10% hydrochloric acid, and then extracted with ethyl acetate. The extract was washed with a saturated aqueous solution of sodium chloride, dried over magnesium sulfate and evaporated under reduced pressure to give 7-[2-[(2,2,2-trifluoroacetamido)-5-chlorothiazol-4-yl]-2-propargyloxyiminoacetamido]cephalosporanic acid (syn isomer, 2.51 g).

IR (Nujol): 3200, 2130, 1790, 1735, 1715, 1665, 1625 cm$^{-1}$.

NMR (DMSO-d$_6$, δ): 2.03 (3H, s), 3.38–3.77 (3H, m), 4.53–5.02 (4H, m), 5.15 (1H, d, J=4.0 Hz), 5.84 (1H, dd, J=4.0 Hz, 8.0 Hz), 9.74 (1H, d, J=8.0 Hz).

EXAMPLE 6

The following compounds were prepared according to the similar manners to those of Examples 1 to 5.

(1) 7-[2-(2-Amino-5-chlorothiazol-4-yl)-2-t-butoxycarbonylmethoxyiminoacetamido]-3-methyl-3-cephem-4-carboxylic acid (syn isomer).

IR (Nujol): 1775, 1725, 1680, 1610 cm$^{-1}$.

(2) 7-[2-(2-Amino-5-chlorothiazol-4-yl)-2-carboxymethoxyiminoacetamido]-3-methyl-3-cephem-4-carboxylic acid (syn isomer).

IR (Nujol): 3400, 3300, 3200, 1775, 1730, 1630 cm$^{-1}$.

(3) 7-[2-(5-Chloro-2-formamidothiazol-4-yl)-2-t-butoxycarbonylmethoxyiminoacetamido]-2-methyl-3-cephem-4-carboxylic acid (syn isomer).

IR (Nujol): 1780, 1720, 1675, 1630 cm$^{-1}$.

NMR (DMSO-d$_6$, δ): 1.26–1.63 (12H, m), 3.76 (1H, m), 4.61 (2H, s), 5.09 (1H, d, J=5.0 Hz), 5.91 (1H, d-d, J=5.0 Hz 9.0 Hz), 6.53 (1H, d, J=6.0 Hz), 8.48 (1H, s), 9.47 (1H, d, J=9 Hz), 12.92 (1H, broad s).

(4) 7-[2-(2-Amino-5-chlorothiazol-4-yl)-2-t-butoxycarbonylmethoxyiminoacetamido]-2-methyl-3-cephem-4-carboxylic acid (syn isomer).

IR (Nujol): 3260, 3170, 1770, 1720, 1680, 1630 cm$^{-1}$.

(5) 7-[2-(2-Amino-5-chlorothiazol-4-yl)-2-carboxymethoxyiminoacetamido]-2-methyl-3-cephem-4-carboxylic acid (syn isomer).

IR (Nujol): 3400, 3260, 3190, 1780, 1730, 1690, 1660, 1620 cm$^{-1}$.

(6) 7-[2-(5-Chloro-2-formamidothiazol-4-yl)-2-t-butoxycarbonylmethoxyiminoacetamido]-3-chloro-3-cephem-4-carboxylic acid (syn isomer).

IR (Nujol): 1775, 1720, 1675 cm$^{-1}$.

(7) 7-[2-(2-Amino-5-chlorothiazol-4-yl)-2-t-butoxycarbonylmethoxyiminoacetamido]-3-chloro-3-cephem-4-carboxylic acid (syn isomer).

IR (Nujol): 3260, 1770, 1715, 1675, 1620 cm$^{-1}$.

(8) 7-[2-(2-Amino-5-chlorothiazol-4-yl)-2-carboxymethoxyiminoacetamido]-3-chloro-3-cephem-4-carboxylic acid (syn isomer).

IR (Nujol): 3400, 3270, 3200, 1780, 1720, 1685, 1655, 1620 cm$^{-1}$.

(9) p-Nitrobenzyl 7-[2-(5-chloro-2-formamidothiazol-4-yl)-2-t-butoxycarbonylmethoxyiminoacetamido]-3-methoxy-3-cephem-4-carboxylate (syn isomer).

IR (Nujol): 1770, 1710, 1670, 1600 cm$^{-1}$.

NMR (DMSO-d$_6$, δ): 1.40 (9H, s), 3.68 (2H, m), 3.77 (3H, s), 4.60 (2H, s), 5.16 (1H, d, J=4.0 Hz), 5.31 (2H, s), 5.69 (1H, d-d, J=4.0 Hz 8.0 Hz), 7.60 (2H, d, J=8.0 Hz), 8.17 (2H, d, J=8.0 Hz), 8.47 (1H, s), 9.46 (1H, d, J=8 Hz), 12.82 (1H, broad s).

(10) 7-[2-(5-Chloro-2-formamidothiazol-4-yl)-2-t-butoxycarbonylmethoxyiminoacetamido]-3-methoxy-3-cephem-4-carboxylic acid (syn isomer).

IR (Nujol): 1770, 1720, 1670 cm$^{-1}$.

(11) 7-[2-(2-Amino-5-chlorothiazol-4-yl)-2-t-butoxycarbonylmethoxyiminoacetamido]-3-methoxy-3-cephem-4-carboxylic acid (syn isomer).

IR (Nujol): 3250, 3150, 1760, 1720, 1670, 1610 cm$^{-1}$.

(12) 7-[2-(2-Amino-5-chlorothiazol-4-yl)-2-carboxymethoxyiminoacetamido]-3-methoxy-3-cephem-4-carboxylic acid (syn isomer).
IR (Nujol): 3280, 3180, 1760, 1670, 1610 cm$^{-1}$.

(13) Benzhydryl 7-[2-(5-chloro-2-trifluoroacetamidothiazol-4-yl)-2-t-butoxycarbonylmethoxyiminoacetamido]-3-methylthiomethyl-3-cephem-4-carboxylate (syn isomer).
IR (Nujol): 3200, 1786, 1727, 1680, 1659, 1605 cm$^{-1}$.
NMR (DMSO-d$_6$, δ): 1.43 (9H, s), 1.80 (3H, s), 3.55 (2H, broad s), 3.60 (2H, broad s), 4.60 (2H, broad s), 5.26 (1H, d, J=5 Hz), 5.93 (1H, dd, J=5 Hz, 9 Hz), 6.93 (1H, s), 7.3 (10H, m), 9.43 (1H, d, J=9 Hz).

(14) 7-[2-(5-Chloro-2-trifluoroacetamidothiazol-4-yl)-2-carboxymethoxyiminoacetamido]-3-methylthiomethyl-3-cephem-4-carboxylic acid (syn isomer).
IR (Nujol): 3230, 1770, 1717, 1656 cm$^{-1}$.

(15) 7-[2-(2-Amino-5-chlorothiazol-4-yl)-2-carboxymethoxyiminoacetamido]-3-methylthiomethyl-3-cephem-4-carboxylic acid (syn isomer).
IR (Nujol): 3400, 3250, 1775, 1718, 1690, 1656 cm$^{-1}$.

(16) 7-[2-(5-Chloro-2-formamidothiazol-4-yl)-2-(3-t-butoxycarbonyl-2-propenyloxyimino)acetamido]-3-cephem-4-carboxylic acid (syn isomer).
IR (Nujol): 1775, 1675 (broad)-cm$^{-1}$.
NMR (DMSO-d$_6$, δ): 1.45 (9H, s), 3.58 (2H, m), 4.86 (2H, d, J=4.0 Hz), 5.12 (1H, d, J=4.0 Hz), 5.88 (1H, d-d, J=4.0 Hz 8.0 Hz), 6.02 (1H, d, J=16.0 Hz), 6.48 (1H, m), 6.90 (1H, d-t, J=16.0 Hz, 4.0 Hz); 8.53 (1H, s), 9.73 (1H, d, J=8.0 Hz), 12.90 (1H, broad s).

(17) 7-[2-(2-Amino-5-chlorothiazol-4-yl)-2-(3-t-butoxycarbonyl-2-propenyloxyimino)]acetamido-3-cephem-4-carboxylic acid (syn isomer).
IR (Nujol): 3280, 3170, 1770, 1680 (broad), 1620 cm$^{-1}$.

(18) 7-[2-(2-Amino-5-chlorothiazol-4-yl)-2-(3-carboxy-2-propenyloxyimino)acetamido]-3-cephem-4-carboxylic acid (syn isomer).
IR (Nujol): 3200, 1775, 1660, 1630 cm$^{-1}$.

(19) 7-[2-(5-Chloro-2-formamidothiazol-4-yl)-2-(3-t-butoxycarbonyl-2-propenyloxyimino)acetamido]-3-(1,3,4-thiadiazol-2-yl)thiomethyl-3-cephem-4-carboxylic acid (syn isomer).
IR (Nujol): 1775, 1680 (broad)-cm$^{-1}$.
NMR (DMSO-d$_6$, δ): 1.44 (9H, s), 3.69 (2H, m), 4.44 (2H, q, J=14.0 Hz), 4.84 (2H, m), 5.16 (1H, d, J=4.0 Hz), 5.84 (1H, d-d, J=4.0 Hz, 8.0 Hz), 5.99 (1H, d, J=16.0 Hz), 6.87 (1H, d-t, J=16.0 Hz, 4.0 Hz), 8.51 (1H, s), 9.51 (1H, s), 9.73 (1H, d, J=8.0 Hz), 12.87 (1H, broad s).

(20) 7-[2-(2-Amino-5-chlorothiazol-4-yl)-2-(3-t-butoxycarbonyl-2-propenyloxyimino)acetamido]-3-(1,3,4-thiadiazol-2-yl)thiomethyl-3-cephem-4-carboxylic acid (syn isomer).
IR (Nujol): 1775, 1680 (broad), 1615 cm$^{-1}$.

(21) 7-[2-(2-Amino-5-chlorothiazol-4-yl)-2-(3-carboxy-2-propenyloxyimino)acetamido]-3-(1,3,4-thiadiazol-2-yl)thiomethyl-3-cephem-4-carboxylic acid (syn isomer).
IR (Nujol): 3300, 3200, 1770, 1670, 1630 cm$^{-1}$.

(22) 7-[2-Allyloxyimino-2-(5-chloro-2-trifluoroacetamido thiazol-4-yl)acetamido]-3-(1-carboxymethyl-1H-tetrazol-5-yl)thiomethyl-3-cephem-4-carboxylic acid (syn isomer).
IR (Nujol): 3210, 1790, 1720, 1660 cm$^{-1}$.
NMR (DMSO-d$_6$, δ): 3.72 (2H, m), 4.40 (2H, q, J=14.0 Hz), 4.72 (2H, d, J=4.0 Hz), 5.08–5.64 (2H, m), 5.16 (1H, d, J=4.0 Hz), 5.34 (2H, s), 5.76–6.49 (1H, m), 5.90 (1H, d-d, J=4.0 Hz 8.0 Hz), 8.97 (2H, broad s), 9.79 (1H, d, J=8.0 Hz).

(23) 7-[2-Allyloxyimino-2-(2-amino-5-chlorothiazol-4-yl)acetamido]-3-(1-carboxymethyl-1H-tetrazol-5-yl)thiomethyl-3-cephem-4-carboxylic acid (syn isomer).
IR (Nujol): 3250, 1765, 1660, 1620 cm$^{-1}$.

(24) 7-[2-(2-Formamido-5-chlorothiazol-4-yl)-2-propargyloxyiminoacetamido]-3-(1,3,4-thiadiazol-2-yl)thiomethyl-3-cephem-4-carboxylic acid (syn isomer).
IR (Nujol): 3250, 2120, 1770, 1760 cm$^{-1}$.
NMR (DMSO-d$_6$, δ): 3.50 (1H, m), 3.73 (2H, m), 4.45 (2H, q, J=14.0 Hz), 4.81 (2H, m), 5.16 (1H, d, J=5.0 Hz), 5.84 (1H, dd, J=5.0 Hz, 8.0 Hz), 8.55 (1H, s), 9.56 (1H, s), 9.73 (1H, d, J=8.0 Hz).

(25) 7-[2-(2-Formamido-5-chlorothiazol-4-yl)-2-(1-tert-butoxycarbonylethoxyimino)acetamido]-3-cephem-4-carboxylic acid (syn isomer).
IR (Nujol): 3150, 1770, 1720, 1670 cm$^{-1}$.
NMR (DMSO-d$_6$, δ): 1.28–1.65 (12H, m), 3.63 (2H, m), 4.65 (1H, q, J=7.0 Hz), 5.14 (1H, d, J=5.0 Hz), 5.90 (1H, dd, J=5.0 Hz, 8.0 Hz), 6.49 (1H, m), 8.54 (1H, s), 9.44, 9.59 (1H, d, J=8.0 Hz), 12.95 (1H, broad s).

(26) 7-[2-(2-Amino-5-chlorothiazol-4-yl)-2-tertbutoxycarbonylmethoxyiminoacetamido]-3-(1,3,4-thiadiazol-2-yl)thiomethyl-3-cephem-4-carboxylic acid (syn isomer).
IR (Nujol): 3150, 1770, 1720, 1670, 1610 cm$^{-1}$.
NMR (DMSO-d$_6$, δ): 1.44 (9H, s), 3.70 (2H, m), 4.44 (2H, m), 4.57 (2H, s), 5.13 (1H, d, J=5 Hz), 5.81 (1H, dd, J=5.0 Hz), 8.0 Hz), 7.41 (2H, broad s), 9.42 (1H, d, J=8.0 Hz), 9.56 (1H, s).

(27) 7-[2-(2-Amino-5-chlorothiazol-4-yl)-2-tertbutoxycarbonylmethoxyiminoacetamido]-3-cephem-4-carboxylic acid (syn isomer), mp 180° to 185° C. (dec.).
IR (Nujol): 3230, 1775, 1728, 1680 cm$^{-1}$.
NMR (DMSO-d$_6$, δ): 1.44 (9H, s), 3.56 (2H, m), 4.56 (2H, s), 5.07 (1H, d, J=5 Hz), 5.82 (1H, dd, J=5 Hz, 8 Hz), 6.46 (1H, m), 9.33 (1H, d, J=8 Hz).

(28) 7-[2-(2-Amino-5-chlorothiazol-4-yl)-2-(1-tertbutoxycarbonylethoxyimino)acetamido]-3-cephem-4-carboxylic acid (syn isomer).
IR (Nujol): 3280, 3180, 1775, 1720, 1670, 1630 cm$^{-1}$.
NMR (DMSO-d$_6$, δ): 1.22–1.60 (12H, m), 3.57 (2H, m), 4.57 (1H, m), 5.09 (1H, d, J=5.0 Hz), 5.82 (1H, m), 6.45 (1H, m), 7.33 (2H, broad s), 9.23, 9.37 (1H, d, J=8.0 Hz).

(29) 7-[2-(2-Amino-5-chlorothiazol-4-yl)-2-propargyloxyiminoacetamido]-3-(1,3,4-thiadiazol-2-yl)thiomethyl-3-cephem-4-carboxylic acid (syn isomer).
IR (Nujol): 3280, 3190, 2100, 1770, 1670, 1620 cm$^{-1}$.
NMR (DMSO-d$_6$, δ): 3.45 (1H, m), 3.68 (2H, q, J=18.0 Hz), 4.44 (2H, q, J=14.0 Hz), 4.72 (2H, m), 5.13 (1H, J=5.0 Hz), 5.77 (1H, dd, J=5.0 Hz, 8.0 Hz), 7.38 (2H, broad s), 9.55 (1H, s), 9.61 (1H, d, J=8.0 Hz).

(30) 7-[2-(2-Formamido-5-chlorothiazol-4-yl)-2-allyloxyiminoacetamido]-3-(1-methyl-1H-tetrazol-5-yl)thiomethyl-3-cephem-4-carboxylic acid (syn isomer).
IR (Nujol): 3200, 1775, 1670 cm$^{-1}$.
NMR (DMSO-d$_6$, δ): 3.73 (2H, m), 3.95 (3H, s), 4.33 (2H, m), 4.69 (2H, m), 5.09–5.58 (2H, m), 5.16 (1H, d, J=5.0 Hz), 5.72–6.33 (1H, m), 5.86 (1H, dd, J=5.0 Hz, 8.0 Hz), 8.55 (1H, s), 9.70 (1H, d, J=8.0 Hz), 12.96 (1H, broad s).

(31) 7-[2-(2-Formamido-5-chlorothiazol-4-yl)-2-allyloxyiminoacetamido]-3-cephem-4-carboxylic acid (syn isomer).
IR (Nujol): 3200, 1780, 1760, 1720, 1670, 1650 cm$^{-1}$.

NMR (DMSO-d$_6$, δ): 3.58 (2H, m), 4.67 (2H, m), 5.04–5.57 (2H, m), 5.10 (1H, d, J=5.0 Hz), 5.72–6.32 (1H, m), 5.87 (1H, dd, J=5.0 Hz, 8.0 Hz), 6.47 (1H, m), 8.53 (1H, s), 9.67 (1H, d, J=8.0 Hz), 12.94 (1H, broad s).

(32) 7-[2-(2-Formamido-5-chlorothiazol-4-yl)-2-allyloxyiminoacetamido]-3-(1,3,4-thiadiazol-2-yl)thiomethyl-3-cephem-4-carboxylic acid (syn isomer).

IR (Nujol): 3160, 1780, 1680 cm$^{-1}$.

NMR (DMSO-d$_6$, δ): 3.71 (2H, m), 4.45 (2H, q, J=14.0 Hz), 4.68 (2H, m), 5.10–5.56 (2H, m), 5.16 (1H, d, J=5.0 Hz), 5.71–6.23 (1H, m), 5.85 ((1H, dd, J=5.0 Hz, 8.0 Hz), 8.54 (1H, s), 9.56 (1H, s), 9.68 (1H, d, J=8.0 Hz), 12.94 (1H, broad s).

(33) 7-[2-(2-Formamido-5-chlorothiazol-4-yl)-2-propargyloxyiminoacetamido]-3-cephem-4-carboxylic acid (syn isomer).

IR (Nujol): 3300, 3200, 1780, 1710, 1670, 1650, 1630 cm$^{-1}$.

NMR (DMSO-d$_6$, δ): 3.40–3.86 (3H, m), 4.80 (2H, d, J=2.0 Hz), 5.12 (1H, d, J=5.0 Hz), 5.88 (1H, dd, J=5.0 Hz, 8.0 Hz), 6.50 (1H, t, J=4.0 Hz), 8.56 (1H, s), 9.73 (1H, d, J=8.0 Hz), 12.97 (1H, broad s).

(34) 7-[2-(2-Formamido-5-chlorothiazol-4-yl)-2-propargyloxyiminoacetamido]-3-(1-methyl-1H-tetrazol-5-yl)thiomethyl-3-cephem-4-carboxylic acid (syn isomer).

IR (Nujol): 3230, 2130, 1780, 1720, 1680 cm$^{-1}$.

NMR (DMSO-d$_6$, δ): 3.51 (1H, m), 3.73 (2H, m), 3.96 (3H, s), 4.34 (2H, m), 4.79 (2H, d, J=2.0 Hz), 5.16 (1H, d, J=5.0 Hz), 5.83 (1H, dd, J=5.0 Hz, 8.0 Hz), 8.56 (1H, s), 9.74 (1H, d, J=8.0 Hz), 12.98 (1H, broad s).

(35) 7-[2-(2-Formamido-5-chlorothiazol-4-yl)-2-propargyloxyiminoacetamido]-3-(5-methyl-1,3,4-thiadiazol-2-yl)thiomethyl-3-cephem-4-carboxylic acid (syn isomer)

IR (Nujol): 2120, 1780, 1715, 1670 cm$^{-1}$.

NMR (DMSO-d$_6$, δ): 2.69 (3H, s), 3.50 (1H, m), 3.68 (2H, m), 4.40 (2H, q, J=14 Hz), 4.81 (2H, m), 5.16 (1H, d, J=5.0 Hz), 5.83 (1H, dd, J=5.0 Hz, 8.0 Hz), 8.56 (1H, s), 9.73 (1H, d, J=8.0 Hz), 12.96 (1H, s)

(36) 7-[2-(2-Formamido-5-chlorothiazol-4-yl)-2-(2-cyclopenten-1-yl)oxyiminoacetamido]-3-(1,3,4-thiadiazol-2-yl)thiomethyl-3-cephem-4-carboxylic acid (syn isomer)

IR (Nujol): 3170, 1770, 1670, 1540 cm$^{-1}$.

NMR (DMSO-d$_6$, δ): 1.86–2.50 (4H, m), 3.62 (2H, AB-q, J=17 Hz), 4.36 (2H, q, J=13 Hz), 5.06 (1H, d, J=5 Hz), 5.20–5.36 (1H, m), 5.56–6.16 (3H, m), 8.42 (1H, s), 9.44 (1H, s), 9.46 (1H, d, J=8 Hz), 12.70 (1H, s).

(37) 7-[2-(2-Amino-5-chlorothiazol-4-yl)-2-propargyloxyiminoacetamido]cephalosporanic acid (syn isomer).

IR (Nujol): 3290, 3200, 2110, 1775, 1720, 1675, 1630 cm$^{-1}$.

(38) 7-[2-(2-Amino-5-chlorothiazol-4-yl)-2-allyloxyiminoacetamido]-3-(1-methyl-1H-tetrazol-5-yl)thiomethyl-3-cephem-4-carboxylic acid (syn isomer)

IR (Nujol): 3300, 3200, 1770, 1670, 1620 cm$^{-1}$.

(39) 7-[2-(2-Amino-5-chlorothiazol-4-yl)-2-allyloxyiminoacetamido]-3-cephem-4-carboxylic acid (syn isomer).

IR (Nujol): 3400, 3250, 3200, 1780, 1665, 1620 cm$^{-1}$.

(40) 7-[2-(2-Amino-5-chlorothiazol-4-yl)-2-allyloxyiminoacetamido]-3-(1,3,4-thiadiazol-2-yl)thiomethyl-3-cephem-4-carboxylic acid (syn isomer).

IR (Nujol): 3300, 3200, 1775, 1670, 1620 cm$^{-1}$.

(41) 7-[2-(2-Amino-5-chlorothiazol-4-yl)-2-propargyloxyiminoacetamido]-3-cephem-4-carboxylic acid (syn isomer)

IR (Nujol): 3400, 3250, 3200, 2100, 1780, 1670, 1620 cm$^{-1}$.

(42) 7-[2-(2-Amino-5-chlorothiazol-4-yl)-2-propargyloxyiminoacetamido]-3-(1-methyl-1H-tetrazol-5-yl)thiomethyl-3-cephem-4-carboxylic acid (syn isomer)

IR (Nujol): 3290, 3200, 2110, 1775, 1675, 1620 cm$^{-1}$.

(43) 7-[2-(2-Amino-5-chlorothiazol-4-yl)-2-propargyloxyiminoacetamido]-3-(5-methyl-1,3,4-thiadiazol-2-yl)thiomethyl-3-cephem-4-carboxylic acid (syn isomer).

IR (Nujol): 3280, 3180, 2100, 1775, 1675, 1620 cm$^{-1}$.

(44) 7-[2-(2-Amino-5-chlorothiazol-4-yl)-2-(2-cyclopenten-1-yl)oxyiminoacetamido]-3-(1,3,4-thiadiazol-2-yl)thiomethyl-3-cephem-4-carboxylic acid (syn isomer)

IR (Nujol): 3300, 3170, 1770, 1670, 1530 cm$^{-1}$.

(45) 7-[2-(5-Chloro-2-trifluoroacetamido-thiazol-4-yl)-2-propargyloxyiminoacetamido]-3-(5-carboxymethyl-4-methylthiazol-2-yl)thiomethyl-3-cephem-4-carboxylic acid (syn isomer).

IR (Nujol): 1770, 1710, 1670 (broad) cm$^{-1}$.

NMR (DMSO-d$_6$, δ): 2.23 (3H, s), 3.47 (1H, m), 3.65 (2H, q, J=19.0 Hz), 3.74 (2H, s), 4.27 (2H, q, J=14.0 Hz), 4.78 (2H, d, J=2.0 Hz), 5.12 (1H, d, J=5.0 Hz), 5.80 (1H, d-d, J=5.0 Hz, 8.0 Hz), 9.73 (1H, d, J=8.0 Hz)

(46) 7-[2-(2-amino-5-chlorothiazol-4-yl)-2-propargyl oxyimino-acetamido]-3-(5-carboxymethyl-4-methylthiazol-2-yl)thiomethyl-3-cephem-4-carboxylic acid (syn isomer).

IR (Nujol): 3280, 3190, 1770, 1675, 1620 cm$^{-1}$.

(47) 7-[2-(5-chloro-2-trifluoroacetamidothiazol-4-yl)-2-allyloxyiminoacetamido]-3-(5-carboxymethyl-4-methylthiazol-2-yl)thiomethyl-3-cephem-4-carboxylic acid (syn isomer).

IR (Nujol): 3170, 1780, 1710, 1655 cm$^{-1}$.

NMR (DMSO-d$_6$, δ): 2.23 (3H, s), 3.65 (2H, q, J=18.0 Hz), 3.74 (2H, s), 4.29 (2H, q, J=14.0 Hz), 4.68 (2H, d, J=5.0 Hz), 5.12~5.54 (2H, m), 5.13 (1H, d, J=4.0 Hz), 5.68~6.32 (2H, m), 9.69 (1H, d, J=8.0 Hz).

(48) 7-[2-(2-amino-5-chlorothiazol-4-yl)-2-allyloxyimino acetamido]-3-(5-carboxymethyl-4-methylthiazol-2-yl)thiomethyl-3-cephem-4-carboxylic acid (syn isomer).

IR (Nujol): 3290, 3190, 1770, 1670, 1620 cm$^{-1}$.

EXAMPLE 7

To a solution of benzhydryl 7-[2-(5-chloro-2-trifluoroacetamidothiazol-4-yl)-2-t-butoxycarbonylmethoxyiminoacetamido]-3-methylthiomethyl-3-cephem-4-carboxylate (syn isomer) (4.0 g) in anisole (4 ml) was added 2,2,2-trifluoroacetic acid (12 ml). The reaction mixture was stirred at ambient temperature for 2.5 hours and then was dropwise added to diisopropyl ether (300 ml). The precipitates were collected by filtration and washed with diisopropyl ether to give.

7-[2-(5-Chloro-2-trifluoroacetamidothiazol-4-yl)-2-carboxymethoxyiminoacetamido]-3-methylthiomethyl-3-cephem-4-carboxylic acid (syn isomer) (2.5 g).

IR (Nujol): 3230, 1770, 1717, 1656 cm$^{-1}$.

NMR (DMSO-d$_6$, δ): 1.98 (3H, s), 3.63 (4H, m), 4.70 (2H, broad s), 5.20 (1H, d, J=5 Hz), 5.83 (1H, dd, J=5 Hz, 9 Hz), 9.56 (1H, d, J=9 Hz).

EXAMPLE 8 p-Nitrobenzyl 7-[2-(5-chloro-2-formamidothiazol-4-yl)-2-t-butoxycarbonylmethoxyiminoacetamido]-3-chloro-3-cephem-4-carboxylate (syn isomer) (6.2 g) was dissolved in a mixed solution of methanol (60 ml), tetrahydrofuran (40 ml) and glacial acetic acid (0.5 ml). After adding 10% palladium carbon (3.1 g) to the solution, the mixture was subjected to catalytic reduction at room temperature under atmospheric pressure. The catalyst was filtered off, and the filtrate was concentrated under reduced pressure. Water and ethyl acetate were added to the residue and the mixture was adjusted to pH 7.5 with saturated aqueous sodium bicarbonate. The separated aqueous layer was adjusted to pH 2.0 with 10% hydrochloric acid and extracted with ethyl acetate. The extract layer was washed with saturated aqueous sodium chloride and dried over magnesium sulfate. The solvent was evaporated to give 7-[2-(5-chloro-2-formamidothiazol-4-yl)-2-t-butoxycarbonylmethoxyiminoacetamido]-3-chloro-3-cephem-4-carboxylic acid (syn isomer) (4.03 g).

IR (Nujol): 1775, 1720, 1675 cm$^{-1}$.

NMR (DMSO-d$_6$, δ): 1.47 (9H, s), 3.85 (2H, q, J=18.0 Hz), 4.66 (2H, s), 5.33 (1H, d, J=5.0 Hz), 5.92 (1H, d-d, J=5.0 Hz 8.0 Hz), 8.57 (1H, s), 9.71 (1H, d, J=8 Hz), 12.94 (1H, broad s).

EXAMPLE 9

The following compounds were prepared according to the similar manners to these of Examples 7 and 8.

(1) 7-[2-(5-Chloro-2-formamidothiazol-4-yl)-2-t-butoxycarbonylmethoxyiminoacetamido]-3-methyl-3-cephem-4-carboxylic acid (syn isomer).

IR (Nujol): 3170, 1775, 1720, 1775 cm$^{-1}$.

(2) 7-[2-(2-Amino-5-chlorothiazol-4-yl)-2-t-butoxycarbonylmethoxyiminoacetamido]-3-methyl-3-cephem-4-carboxylic acid (syn isomer).

IR (Nujol): 1775, 1725, 1680, 1610 cm$^{-1}$.

(3) 7-[2-(2-Amino-5-chlorothiazol-4-yl)-2-carboxymethoxyiminoacetamido]-3-methyl-3-cephem-4-carboxylic acid (syn isomer).

IR (Nujol): 3400, 3300, 3200, 1775, 1730, 1630 cm$^{-1}$.

(4) 7-[2-(5-Chloro-2-formamidothiazol-4-yl)-2-t-butoxycarbonylmethoxyiminoacetamido]-2-methyl-3-cephem-4-carboxylic acid (syn isomer).

IR (Nujol): 1780, 1720, 1675, 1630 cm$^{-1}$.

(5) 7-[2-(2-Amino-5-chlorothiazol-4-yl)-2-t-butoxycarbonylmethoxyiminoacetamido]-2-methyl-3-cephem-4-carboxylic acid (syn isomer).

IR (Nujol): 3260, 3170, 1770, 1720, 1680, 1630 cm$^{-1}$.

(6) 7-[2-(2-Amino-5-chlorothiazol-4-yl)-2-carboxymethoxyiminoacetamido]-2-methyl-3-cephem-4-carboxylic acid (syn isomer).

IR (Nujol): 3400, 3260, 3190, 1780, 1730, 1690, 1660, 1620 cm$^{-1}$.

(7) 7-[2-(2-Amino-5-chlorothiazol-4-yl)-2-t-butoxycarbonylmethoxyiminoacetamido]-3-chloro-3-cephem-4-carboxylic acid (syn isomer).

IR (Nujol): 3260, 1770, 1715, 1675, 1620 cm$^{-1}$.

(8) 7-[2-(2-Amino-5-chlorothiazol-4-yl)-2-carboxymethoxyiminoacetamido]-3-chloro-3-cephem-4-carboxylic acid (syn isomer).

IR (Nujol): 3400, 3270, 3200, 1780, 1720, 1685, 1655, 1620 cm$^{-1}$.

(9) 7-[2-(5-Chloro-2-formamidothiazol-4-yl)-2-t-butoxycarbonylmethoxyiminoacetamido]-3-methoxy-3-cephem-4-carboxylic acid (syn isomer).

IR (Nujol): 1770, 1720, 1670 cm$^{-1}$.

NMR (DMSO-d$_6$, δ): 1.43 (9H, s), 3.61 (2H, s), 3.74 (3H, s), 4.62 (2H, s), 5.14 (1H, d, J=4.0 Hz), 5.66 (1H, d-d, J=4.0 Hz 8.0 Hz), 8.52 (1H, s), 9.45 (1H, d, J=8.0 Hz), 12.87 (1H, broad s).

(10) 7-[2-(2-Amino-5-chlorothiazol-4-yl)-2-t-butoxycarbonylmethoxyiminoacetamido]-3-methoxy-3-cephem-4-carboxylic acid (syn isomer).

IR (Nujol): 3250, 3150, 1760, 1720, 1670, 1610 cm$^{-1}$.

(11) 7-[2-(2-Amino-5-chlorothiazol-4-yl)-2-carboxymethoxyiminoacetamido]-3-methoxy-3-cephem-4-carboxylic acid (syn isomer).

IR (Nujol): 3280, 3180, 1760, 1670, 1610 cm$^{-1}$.

(12) 7-[2-(2-Amino-5-chlorothiazol-4-yl)-2-carboxymethoxyiminoacetamido]-3-methylthiomethyl-3-cephem-4-carboxylic acid (syn isomer).

IR (Nujol): 3400, 3250, 1775, 1718, 1690, 1656 cm$^{-1}$.

(13) 7-[2-(5-Chloro-2-formamidothiazol-4-yl)-2-(3-t-butoxycarbonyl-2-propenyloxyimino)acetamido]-3-cephem-4-carboxylic acid (syn isomer).

IR (Nujol): 1775, 1675 (broad)-cm$^{-1}$.

(14) 7-[2-(2-Amino-5-chlorothiazol-4-yl)-2-(3-t-butoxycarbonyl-2-propenyloxyimino)acetamido]-3-cephem-4-carboxylic acid (syn isomer).

IR (Nujol): 3280, 3170, 1770, 1680 (broad), 1620 cm$^{-1}$.

(15) 7-[2-(2-Amino-5-chlorothiazol-4-yl)-2-(3-carboxy-2-propenyloxyimino)acetamido]-3-cephem-4-carboxylic acid (syn isomer)

IR (Nujol): 3200, 1775, 1660, 1630 cm$^{-1}$.

(16) 7-[2-(5-Chloro-2-formamidothiazol-4-yl)-2-(3-t-butoxycarbonyl-2-propenyloxyimino)acetamido]-3-(1,3,4-thiadiazol-2-yl)thiomethyl-3-cephem-4-carboxylic acid (syn isomer).

IR (Nujol): 1775, 1680 (broad)-cm$^{-1}$.

(17) 7-[2-(2-Amino-5-chlorothiazol-4-yl)-2-(3-t-butoxycarbonyl-2-propenyloxyimino)acetamido]-3-(1,3,4-thiadiazol-2-yl)thiomethyl-3-cephem-4-carboxylic acid (syn isomer).

IR (Nujol): 1775, 1680 (broad), 1615-cm$^{-1}$.

(18) 7-[2-(2-Amino-5-chlorothiazol-4-yl)-2-(3-carboxy-2-propenyloxyimino)acetamido]-3-(1,3,4-thiadiazol-2-yl)thiomethyl-3-cephem-4-carboxylic acid (syn isomer).

IR (Nujol): 3300, 3200, 1770, 1670, 1630 cm$^{-1}$.

(19) 7-[2-Allyloxyimino-2-(5-chloro-2-trifluoroacetamidothiazol-4-yl)acetamido]-3-(1-carboxymethyl-1H-tetrazol-5-yl)thiomethyl-3-cephem-4-carboxylic acid (syn isomer).

IR (Nujol): 3210, 1790, 1720, 1660 cm$^{-1}$.

(20) 7-[2-Allyloxyimino-2-(2-amino-5-chlorothiazol-4-yl)acetamido]-3-(1-carboxymethyl-1H-tetrazol-5-yl)thiomethyl-3-cephem-4-carboxylic acid (syn isomer).

IR (Nujol): 3250, 1765, 1660, 1620 cm$^{-1}$.

(21) 7-[2-(2-formamido-5-chlorothiazol-4-yl)-2-tert-butoxycarbonylmethoxyiminoacetamido]-3-(1,3,4-thiadiazol-2-yl)thiomethyl-3-cephem-4-carboxylic acid (syn isomer)

IR (Nujol): 1775, 1710, 1670 cm$^{-1}$.

(22) 7-[2-(2-formamido-5-chlorothiazol-4-yl)-2-tert-butoxycarbonylmethoxyiminoacetamido]-3-cephem-4-carboxylic acid (syn isomer) mp 145° to 149° C. (dec.).

IR (Nujol): 3200, 1775, 1720, 1670 cm$^{-1}$.

(23) 7-[2-(2-Formamido-5-chlorothiazol-4-yl)-2-propargyloxyiminoacetamido]-3-(1,3,4-thiadiazol-2-yl)thiomethyl-3-cephem-4-carboxylic acid (syn isomer).

(24) 7-[2-(2-Formamido-5-chlorothiazol-4-yl)-2-(1-tert-butoxycarbonylethoxyimino)acetamido]-3-cephem-4-carboxylic acid (syn isomer).
IR (Nujol): 3150, 1770, 1720, 1670 cm$^{-1}$.

(25) 7-[2-(2-Amino-5-chlorothiazol-4-yl)-2-tertbutoxycarbonylmethoxyiminoacetamido]-3-(1,3,4-thiadiazol-2-yl)thiomethyl-3-cephem-4-carboxylic acid (syn isomer).
IR (Nujol): 3150, 1770, 1720, 1670, 1610 cm$^{-1}$.

(26) 7-[2-(2-Amino-5-chlorothiazol-4-yl)-2-tertbutoxycarbonylmethoxyiminoacetamido]-3-cephem-4-carboxylic acid (syn isomer), mp 180° to 185° C. (dec.).
IR (Nujol): 3230, 1775, 1728, 1680 cm$^{-1}$.

(27) 7-[2-(2-Amino-5-chlorothiazol-4-yl)-2-(1-tertbutoxycarbonylethoxyimino)acetamido]-3-cephem-4-carboxylic acid (syn isomer).
IR (Nujol): 3280, 3180, 1775, 1720, 1670, 1630 cm$^{-1}$.

(28) 7-[2-(2-Amino-5-chlorothiazol-4-yl)-2-propargyloxyiminoacetamido]-3-(1,3,4-thiadiazol-2-yl)thiomethyl-3-cephem-4-carboxylic acid (syn isomer).
IR (Nujol): 3280, 3190, 2100, 1770, 1670, 1620 cm$^{-1}$.

(29) 7-[2-(2-Amino-5-chlorothiazol-4-yl)-2-carboxymethoxyiminoacetamido]-3-(1,3,4-thiadiazol-2-yl)thiomethyl-3-cephem-4-carboxylic acid (syn isomer).
IR (Nujol): 3360, 3240, 1775, 1675, 1630 cm$^{-1}$.

(30) 7-[2-(2-Amino-5-chlorothiazol-4-yl)-2-carboxymethoxyiminoacetamido]-3-cephem-4-carboxylic acid (syn isomer), mp 165° to 167° C. (dec.).
IR (Nujol): 3260, 1760, 1670 cm$^{-1}$.

(31) 7-[2-(2-Amino-5-chlorothiazol-4-yl)-2-(1-carboxyethoxyimino)acetamido]-3-cephem-4-carboxylic acid (syn isomer).
IR (Nujol): 3250, 3190, 1775, 1665, 1620 cm$^{-1}$.

(32) 7-[2-(2,2,2-trifluoroacetamido)-5-chlorothiazol-4-yl]-[2-propargyloxyiminoacetamido]cephalosporanic acid (syn isomer, 2.51 g).
IR (Nujol): 3200, 2130, 1790, 1735, 1715, 1665, 1625 cm$^{-1}$.

(33) 7-[2-(2-Formamido-5-chlorothiazol-4-yl)-2-allyloxyiminoacetamido]-3-(1-methyl-1H-tetrazol-5-yl)thiomethyl-3-cephem-4-carboxylic acid (syn isomer).
IR (Nujol): 3200, 1775, 1670 cm$^{-1}$.

(34) 7-[2-(2-Formamido-5-chlorothiazol-4-yl)-2-allyloxyiminoacetamido]-3-cephem-4-carboxylic acid (syn isomer).
IR (Nujol): 3200, 1780, 1760, 1720, 1670, 1650 cm$^{-1}$.

(35) 7-[2-(2-Formamido-5-chlorothiazol-4-yl)-2-allyloxyiminoacetamido]-3-(1,3,4-thiadiazol-2-yl)thiomethyl-3-cephem-4-carboxylic acid (syn isomer).
IR (Nujol): 3160, 1780, 1680 cm$^{-1}$.

(36) 7-[2-(2-Formamido-5-chlorothiazol-4-yl)-2-propargyloxyiminoacetamido]-3-cephem-4-carboxylic acid (syn isomer).
IR (Nujol): 3300, 3200, 1780, 1710, 1670, 1650, 1630 cm$^{-1}$.

(37) 7-[2-(2-Formamido-5-chlorothiazol-4-yl)-2-propargyloxyiminoacetamido]-3-(1methyl-1H-tetrazol-5-yl)thiomethyl-3-cephem-4-carboxylic acid (syn isomer).
IR (Nujol): 3230, 2130, 1780, 1720, 1680 cm$^{-1}$.

(38) 7-[2-(2-Formamido-5-chlorothiazol-4-yl)-2-propargyloxyiminoacetamido]-3-(5-methyl-1,3,4-thiadiazol-2-yl)thiomethyl-3-cephem-4-carboxylic acid (syn isomer)
IR (Nujol): 2120, 1780, 1715, 1670 cm$^{-1}$.

(39) 7-[2-(2-Formamido-5-chlorothiazol-4-yl)-2-(2-cyclopenten-1-yl)oxyiminoacetamido]-3-(1,3,4-thiadiazol-2-yl)thiomethyl-3-cephem-4-carboxylic acid (syn isomer)
IR (Nujol): 3170, 1770, 1670, 1540 cm$^{-1}$.

(40) 7-[2-(2-Amino-5-chlorothiazol-4-yl)-2-propargyloxyiminoacetamido]cephalosporanic acid (syn isomer).
IR (Nujol): 3290, 3200, 2110, 1775, 1720, 1675, 1630 cm$^{-1}$.

(41) 7-[2-(2-Amino-5-chlorothiazol-4-yl)-2-allyloxyiminoacetamido]-3-(1-methyl-1H-tetrazol-5-yl)thiomethyl-3-cephem-4-carboxylic acid (syn isomer)
IR (Nujol): 3300, 3200, 1770, 1670, 1620 cm$^{-1}$.

(42) 7-[2-(2-Amino-5-chlorothiazol-4-yl)-2-allyloxyiminoacetamido]-3-cephem-4-carboxylic acid (syn isomer).
IR (Nujol): 3400, 3250, 3200, 1780, 1665, 1620 cm$^{-1}$.

(43) 7-[2-(2-Amino-5-chlorothiazol-4-yl)-2-allyloxyiminoacetamido]-3-(1,3,4-thiadiazol-2-yl)thiomethyl-3-cephem-4-carboxylic acid (syn isomer).
IR (Nujol): 3300, 3200, 1775, 1670, 1620 cm$^{-1}$.

(44) 7-[2-(2-Amino-5-chlorothiazol-4-yl)-2-propargyloxyiminoacetamido]-3-cephem-4-carboxylic acid (syn isomer)
IR (Nujol): 3400, 3250, 3200, 2100, 1780, 1670, 1620 cm$^{-1}$.

(45) 7-[2-(2-Amino-5-chlorothiazol-4-yl)-2-propargyloxyiminoacetamido]-3-(1-methyl-1H-tetrazol-5-yl)thiomethyl-3-cephem-4-carboxylic acid (syn isomer)
IR (Nujol): 3290, 3200, 2110, 1775, 1675, 1620 cm$^{-1}$.

(46) 7-[2-(2-Amino-5-chlorothiazol-4-yl)-2-propargyloxyiminoacetamido]-3-(5-methyl-1,3,4-thiadiazol-2-yl)thiomethyl-3-cephem-4-carboxylic acid (syn isomer).
IR (Nujol): 3280, 3180, 2100, 1775, 1675, 1620 cm$^{-1}$.

(47) 7-[2-(2-Amino-5-chlorothiazol-4-yl)-2-(2-cyclopenten-1-yl)oxyiminoacetamido]-3-(1,3,4-thiadiazol-2-yl)thiomethyl-3-cephem-4-carboxylic acid (syn isomer)
IR (Nujol): 3300, 3170, 1770, 1670, 1530 cm$^{-1}$.

(48) 7-[2-(5-Chloro-2-trifluoroacetamido-thiazol-4-yl)-2-propargyloxyiminoacetamido]-3-(5-carboxymethyl-4-methylthiazol-2-yl)thiomethyl-3-cephem-4-carboxylic acid (syn isomer).
IR (Nujol): 1770, 1710, 1670 (broad) cm$^{-1}$.

(49) 7-[2-(2-amino-5-chlorothiazol-4-yl)-2-propargyl oxyimino-acetamido]-3-(5-carboxymethyl-4-methylthiazol-2-yl)thiomethyl-3-cephem-4-carboxylic acid (syn isomer).
IR (Nujol): 3280, 3190, 1770, 1675, 1620 cm$^{-1}$.

(50) 7-[2-(5-chloro-2-trifluoroacetamidothiazol-4-yl)-2-allyloxyiminoacetamido]-3-(5-carboxymethyl-4-methylthiazol-2-yl)thiomethyl-3-cephem-4-carboxylic acid (syn isomer).
IR (Nujol): 3170, 1780, 1710, 1655 cm$^{-1}$.

(51) 7-[2-(2-amino-5-chlorothiazol-4-yl)-2-allyloxyiminoacetamido]-3-(5-carboxymethyl-4-methylthiazol-2-yl)thiomethyl-3-cephem-4-carboxylic acid (syn isomer).
IR (Nujol): 3290, 3190, 1770, 1670, 1620 cm$^{-1}$.

EXAMPLE 10

A mixture of 7-[2-(5-chloro-2-formamidothiazol)-4-yl)-2-t-butoxycarbonylmethoxyiminoacetamido]-3-methyl-3-cephem-4-carboxylic acid (syn isomer) (2.9 g) in methanol (30 ml) and conc. hydrochloric acid (1.1 g) were stirred for 3 hours at ambient temperature. The reaction mixture was added to a mixture of ethyl acetate and water and adjusted to pH 7.5 with saturated aqueous sodium bicarbonate. The separated aqueous layer was adjusted to pH 3.0 with 10% aqueous hydrochloric acid and saturated with sodium chloride. The acidic mixture was extracted with ethyl acetate-tetrahydrofuran (1:1). The extract layer was washed with saturated aqueous sodium chloride, dried over magnesium sulfate and evaporated to give 7-[2-(2-amino-5-chlorothiazol-4-yl)-2-t-butoxycarbonylmethoxyiminoacetamido]-3-methyl-3-cephem-4-carboxylic acid (syn isomer) (2.41 g).

IR (Nujol): 1775, 1725, 1680, 1610 cm$^{-1}$.

NMR (DMSO-$d_6$, $\delta$): 1.43 (9H, s), 2.02 (3H, s), 3.45 (2H, m), 4.58 (2H, s), 5.07 (1H, d, J=4.0 Hz), 5.72 (1H, d-d, J=4.0 Hz 8.0 Hz), 7.36 (2H, broad s), 9.29 (1H, d).

EXAMPLE 11

A solution of 7-[2-(5-chloro-2-trifluoroacetamidothiazol-4-yl)-2-carboxymethoxyiminoacetamido]-3-methylthiomethyl-3-cephem-4-carboxylic acid (syn isomer) (2.5 g) and sodium acetate (5.6 g) in water (25 ml) was stirred at ambient temperature for 13 hours. The resultant solution was washed with ethyl acetate and the separated aqueous layer was treated with activecharcoal. And the aqueous layer was adjusted to pH 2.3 with 10% hydrochloric acid. The precipitates were collected by filtration and washed with water. The precipitates were dried under reduced pressure to give 7-[2-(2-amino-5-chlorothiazol-4-yl)-2-carboxymethoxyiminoacetamido]-3-methylthiomethyl-3-cephem-4-carboxylic acid (syn isomer) (1.7 g).

IR (Nujol): 3400, 3250, 1775, 1718, 1690, 1656 cm$^{-1}$.

NMR (DMSO-$d_6$, $\delta$): 2.00 (3H, s), 3.60 (4H, broad s), 4.63 (2H, broad s), 5.19 (1H, d, J=5 Hz), 5.80 (1H, dd, J=5 Hz 8 Hz), 9.43 (1H, d, J=8 Hz).

EXAMPLE 12

A mixture of 7-[2-(2-formamido-5-chlorothiazol-4-yl)-2-tert-butoxycarbonylmethoxyiminoacetamido]-3-(1,3,4-thiadiazol-2-yl)thiomethyl-3-cephem-4-carboxylic acid (syn isomer) (3.6 g) in methanol (36 ml) and conc. hydrochloric acid (1.1 g) was stirred for 3.0 hours at ambient temperature. The reaction mixture was added to water and ethyl acetate, and adjusted to pH 7.5 with a saturated aqueous solution of sodium bicarbonate. The aqueous layer was separated and adjusted to pH 3.0 with 10% aqueous hydrochloric acid, and then extracted with ethyl acetate. The extract was washed with a saturated aqueous solution of sodium chloride, dried over magnesium sulfate, and evaporated to give 7-[2-(2-amino-5-chlorothiazol-4-yl)-2-tert-butoxycarbonylmethoxyiminoacetamido]-3-(1,3,4-thiadiazol-2-yl)thiomethyl-3-cephem-4-carboxylic acid (syn isomer) (2.62 g).

IR (Nujol): 3150, 1770, 1720, 1670, 1610 cm$^{-1}$.

NMR (DMSO-$d_6$, $\delta$): 1.44 (9H, s), 3.70 (2H, m), 4.44 (2H, m), 4.57 (2H, s), 5.13 (1H, d, J=5.0 Hz), 5.81 (1H, dd, J=5.0 Hz, 8.0 Hz), 7.41 (2H, broad s), 9.42 (1H, d, J=8.0 Hz), 9.56 (1H, s).

EXAMPLE 13

To a solution of 7-[2-(2-formamido-5-chlorothiazol-4-yl)-2-tert-butoxycarbonylmethoxyiminoacetamido]-3-cephem-4-carboxylic acid (syn isomer) (2.1 g) in methanol (50 ml) was added conc. hydrochloric acid (1.35 ml) at 32° to 35° C. The mixture was stirred for an hour at the same temperature. The resultant solution was adjusted to pH 5.0 with a saturated aqueous solution of sodium bicarbonate. After removing the solvent, the residual insoluble precipitates were collected by filtration. The precipitates were washed with water and dried over phosphorus pentoxide to give 7-[2-(2-amino-5-chlorothiazol-4-yl)-2-tert-butoxycarbonylmethoxyiminoacetamido]-3-cephem-4-carboxylic acid (syn isomer) (1.8 g), mp 180° to 185° C. (dec.).

IR (Nujol): 3230, 1775, 1728, 1680 cm$^{-1}$.

NMR (DMSO-$d_6$, $\delta$): 1.44 (9H, s), 3.56 (2H, m), 4.56 (2H, s), 5.07 (1H, d, J=5 Hz), 5.82 (1H, dd, J=5 Hz, 8 Hz), 6.46 (1H, m), 9.33 (1H, d, J=8 Hz).

EXAMPLE 14

A mixture of 7-[2-[2-(2,2,2-trifluoroacetamido)-5-chlorothiazol-4-yl]-2-propargyloxyiminoacetamido]-cephalosporanic acid (syn isomer, 2.4 g) and sodium acetate (6.3 g) in water (60 ml) and tetrahydrofuran (2 ml) was stirred for 20 hours at ambient temperature. The reaction mixture was adjusted to pH 3.0 with 10% hydrochloric acid and extracted with a mixture of ethyl acetate and tetrahydrofuran (1:1). The organic layer was separated, washed with a saturated aqueous solution of sodium chloride and dried over magnesium sulfate. The solution was evaporated under reduced pressure to give 7-[2-(2-amino-5-chlorothiazol-4-yl)-2-propargyloxyiminoacetamido]cephalosporanic acid (syn isomer, 1.09 g).

IR (Nujol): 3290, 3200, 2110, 1775, 1720, 1675, 1630 cm$^{-1}$.

NMR (DMSO-$d_6$, $\delta$): 2.04 (3H, s), 3.41–3.66 (3H, m), 4.51–5.00 (4H, m), 5.13 (1H, d, J=4.0 Hz), 5.78 (1H, dd, J=4.0 Hz, 8.0 Hz), 7.31 (2H, broad s), 9.59 (1H, d, J=8.0 Hz).

EXAMPLE 15

A mixture of 7-[2-(2-formamido-5-chlorothiazol-4-yl)-2-allyloxyiminoacetamido]-3-(1-methyl-1H-tetrazol-5-yl)thiomethyl-3-cephem-4-carboxylic acid (syn isomer, 1.5 g) in methanol (15 ml), and conc. hydrochloric acid (0.52 g) and tetrahydrofuran (3.0 ml) was stirred for 3.0 hours at ambient temperature. The reaction mixture was added to water and ethyl acetate, and adjusted to pH 7.5 with a saturated aqueous solution of sodium bicarbonate. The aqueous layer was separated and adjusted to pH 3.0 with 10% hydrochloric acid, and then extracted with ethyl acetate. The extract was washed with a saturated aqueous solution of sodium chloride, dried over magnesium sulfate, and evaporated under reduced pressure to give 7-[2-(2-amino-5-chlorothiazol-4-yl)-2-allyloxyiminoacetamido]-3-(1-methyl-1H-tetrazol-5-yl)thiomethyl-3-cephem-4-carboxylic acid (syn isomer, 1.02 g).

IR (Nujol): 3300, 3200, 1770, 1670, 1620 cm$^{-1}$.

NMR (DMSO-$d_6$, $\delta$): 3.68 (2H, m), 3.93 (3H, s), 4.30 (2H, m), 4.59 (2H, d, J=5.0 Hz), 5.06–5.55 (2H, m), 5.09 (1H, d, J=5.0 Hz), 5.63–6.29 (1H, m), 5.76 (1H, dd, J=5.0 Hz, 8.0 Hz), 7.30 (2H, broad s), 9.50 (1H, d, J=8.0 Hz).

EXAMPLE 16

The following compounds were prepared according to the similar manners to those of Examples 10 to 15.

(1) 7-[2-(2-Amino-5-chlorothiazol-4-yl)-2-carboxymethoxyiminoacetamido]-3-methyl-3-cephem-4-carboxylic acid (syn isomer).

IR (Nujol): 3400, 3300, 3200, 1775, 1730, 1630 cm$^{-1}$.

(2) 7-[2-(2-Amino-5-chlorothiazol-4-yl)-2-t-butoxycarbonylmethoxyiminoacetamido]-2-methyl-3-cephem-4-carboxylic acid (syn isomer).

IR (Nujol): 3260, 3170, 1770, 1720, 1680, 1630 cm$^{-1}$.

NMR (DMSO-d$_6$, δ): 1.28–1.61 (12H, m), 3.65 (1H, m), 4.55 (2H, s), 5.07 (1H, d, J=4.0 Hz), 5.87 (1H, d-d, J=4 Hz, 8.0 Hz), 6.52 (1H, d, J=6.0 Hz), 7.32 (2H, broad s), 9.31 (1H, d, J=8.0 Hz).

(3) 7-[2-(2-Amino-5-chlorothiazol-4-yl)-2-carboxymethoxyiminoacetamido]-2-methyl-3-cephem-4-carboxylic acid (syn isomer).

IR (Nujol): 3400, 3260, 3190, 1780, 1730, 1690, 1660, 1620 cm$^{-1}$.

(4) 7-[2-(2-Amino-5-chlorothiazol-4-yl)-2-t-butoxycarbonylmethoxyiminoacetamido]-3-chloro-3-cephem-4-carboxylic acid (syn isomer).

IR (Nujol): 3260, 1770, 1715, 1675, 1620 cm$^{-1}$.

NMR (DMSO-d$_6$, δ): 1.43 (9H, s), 3.77 (2H, q, J=9.0 Hz), 4.53 (2H, s), 5.21 (1H, d, J=4.0 Hz), 5.81 (1H, d-d, J=4.0 Hz, 8.0 Hz), 7.32 (2H, broad s), 9.47 (1H, d, J=8.0 Hz).

(5) 7-[2-(2-Amino-5-chlorothiazol-4-yl)-2-carboxymethoxyiminoacetamido]-3-chloro-3-cephem-4-carboxylic acid (syn isomer).

IR (Nujol): 3400, 3270, 3200, 1780, 1720, 1685, 1655, 1620 cm$^{-1}$.

(6) 7-[2-(2-Amino-5-chlorothiazol-4-yl)-2-t-butoxycarbonylmethoxyiminoacetamido]-3-methoxy-3-cephem-4-carboxylic acid (syn isomer).

IR (Nujol): 3250, 3150, 1760, 1720, 1670, 1610 cm$^{-1}$.

NMR (DMSO-d$_6$, δ): 1.46 (9H, s), 3.62 (2H, s), 3.78 (3H, s), 4.59 (2H, s), 5.14 (1H, d, J=4.0 Hz), 5.65 (1H, d-d, J=4.0 Hz, 8.0 Hz), 7.37 (2H, broad s), 9.35 (1H, d, J=8.0 Hz).

(7) 7-[2-(2-Amino-5-chlorothiazol-4-yl)-2-carboxymethoxyiminoacetamido]-3-methoxy-3-cephem-4-carboxylic acid (syn isomer).

IR (Nujol): 3280, 3180, 1760, 1670, 1610 cm$^{-1}$.

(8) 7-[2-(2-Amino-5-chlorothiazol-4-yl)-2-(3-t-butoxycarbonyl-2-propenyloxyimino)acetamido]-3-cephem-4-carboxylic acid (syn isomer).

IR (Nujol): 3280, 3170, 1770, 1680 (broad), 1620 cm$^{-1}$.

NMR (DMSO-d$_6$, δ): 1.41 (9H, s), 3.56 (2H, m), 4.77 (2H, d, J=4.0 Hz), 5.08 (1H, d, J=5.0 Hz), 5.83 (1H, d-d, J=5.0 Hz, 8.0 Hz), 5.96 (1H, d, J=16.0 Hz), 6.46 (1H, m), 6.86 (1H, d-t, J=16.0 Hz, 4.0 Hz), 7.34 (2H, broad s), 9.63 (1H, d, J=8.0 Hz).

(9) 7-[2-(2-Amino-5-chlorothiazol-4-yl)-2-(3-carboxy-2-propenyloxyimino)acetamido]-3-cephem-4-carboxylic acid (syn isomer).

IR (Nujol): 3200, 1775, 1660, 1630 cm$^{-1}$.

(10) 7-[2-(2-Amino-5-chlorothiazol-4-yl)-2-(3-t-butoxycarbonyl-2-propenyloxyimino)acetamido]-3-(1,3,4-thiadiazol-2-yl)thiomethyl-3-cephem-4-carboxylic acid (syn isomer).

IR (Nujol): 1775, 1680 (broad), 1615 cm$^{-1}$.

NMR (DMSO-d$_6$, δ): 1.43 (9H, s), 3.64 (2H, m), 4.43 (2H, q, J=14.0 Hz), 4.76 (2H, m), 5.11 (1H, d, J=5.0 Hz), 5.77 (1H, d-d, J=5.0 Hz 8.0 Hz), 5.94 (1H, d, J=16.0 Hz), 6.84 (1H, d-t, J=16.0 Hz, 4.0 Hz), 7.31 (2H, broad s), 9.48 (1H, s), 9.59 (1H, d, J=8.0 Hz).

(11) 7-[2-(2-Amino-5-chlorothiazol-4-yl)-2-(3-carboxy-2-propenyloxyimino)acetamido]-3-(1,3,4-thiadiazol-2-yl)thiomethyl-3-cephem-4-carboxylic acid (syn isomer).

IR (Nujol): 3300, 3200, 1770, 1670, 1630 cm$^{-1}$.

(12) 7-[2-Allyloxyimino-2-(2-amino-5-chlorothiazol-4-yl)acetamido]-3-(1-carboxymethyl-1H-tetrazol-5-yl)thiomethyl-3-cephem-4-carboxylic acid (syn isomer).

IR (Nujol): 3250, 1765, 1660, 1620 cm$^{-1}$.

NMR (DMSO-d$_6$, δ): 3.68 (2H, broad s), 4.38 (2H, q, J=14.0 Hz), 4.62 (2H, d, J=5.0 Hz), 5.04–5.57 (3H, m), 5.31 (2H, s), 5.67–6.32 (1H, m), 5.79 (1H, d-d, J=5.0 Hz 8.0 Hz), 7.37 (2H, broad s), 9.59 (1H, d, J=8.0 Hz).

(13) 7-[2-(2-Amino-5-chlorothiazol-4-yl)-2-(1-tert-butoxycarbonylethoxyimino)acetamido]-3-cephem-4-carboxylic acid (syn isomer).

IR (Nujol): 3280, 3180, 1775, 1720, 1670, 1630 cm$^{-1}$.

NMR (DMSO-d$_6$, δ): 1.22–1.60 (12H, m), 3.57 (2H, m), 4.57 (1H, m), 5.09 (1H, d, J=5.0 Hz), 5.82 (1H, m), 6.45 (1H, m), 7.33 (2H, broad s), 9.23, 9.37 (1H, d, J=8.0 Hz).

(14) 7-[2-(2-Amino-5-chlorothiazol-4-yl)-2-propargyloxyiminoacetamido]-3-(1,3,4-thiadiazol-2-yl)thiomethyl-3-cephem-4-carboxylic acid (syn isomer).

IR (Nujol): 3280, 3190, 2100, 1770, 1670, 1620 cm$^{-1}$.

NMR (DMSO-d$_6$, δ): 3.45 (1H, m), 3.68 (2H, q, J=18.0 Hz), 4.44 (2H, q, J=14.0 Hz), 4.72 (2H, m), 5.13 (1H, d, J=5.0 Hz), 5.77 (1H, dd, J=5.0 Hz, 8.0 Hz), 7.38 (2H, broad s), 9.55 (1H, s), 9.61 (1H, d, J=8.0 Hz).

(15) 7-[2-(2-Amino-5-chlorothiazol-4-yl)-2-carboxymethoxyiminoacetamido]-3-(1,3,4-thiadiazol-2-yl)thiomethyl-3-cephem-4-carboxylic acid (syn isomer).

IR (Nujol): 3360, 3240, 1775, 1675, 1630 cm$^{-1}$.

NMR (DMSO-d$_6$, δ): 3.69 (2H, q, J=18.0 Hz), 4.40 (2H, q, J=13.0 Hz), 4.63 (2H, s), 5.14 (1H, d, J=4.0 Hz), 5.82 (1H, dd, J=4.0 Hz), 7.40 (2H, broad s), 9.45 (1H, d, J=8.0 Hz), 9.56 (1H, s).

(16) 7-[2-(2-Amino-5-chlorothiazol-4-yl)-2-carboxymethoxyiminoacetamido]-3-cephem-4-carboxylic acid (syn isomer), mp 165° to 167° C. (dec.).

IR (Nujol): 3260, 1760, 1670 cm$^{-1}$.

NMR (DMSO-d$_6$, δ): 3.66 (2H, m), 4.62 (2H, broad s), 5.08 (1H, d, J=5 Hz), 5.83 (1H, dd, J=5 Hz, 9 Hz), 6.49 (1H, m), 9.50 (1H, d, J=9 Hz).

(17) 7-[2-(2-Amino-5-chlorothiazol-4-yl)-2-(1-carboxyethoxyimino)acetamido]-3-cephem-4-carboxylic acid (syn isomer).

IR (Nujol): 3250, 3190, 1775, 1665, 1620 cm$^{-1}$.

NMR (DMSO-d$_6$, δ): 1.38, 1.43 (3H, d, J=7.0 Hz), 3.60 (2H, m), 4.66 (1H, m), 5.10 (1H, d, J=5.0 Hz), 5.85 (1H, dd, J=5.0 Hz, 8.0 Hz), 6.46 (1H, m), 9.29, 9.38 (1H, d, J=8.0 Hz).

(18) 7-[2-(2-Amino-5-chlorothiazol-4-yl)-2-allyloxyiminoacetamido]-3-cephem-4-carboxylic acid (syn isomer).

IR (Nujol): 3400, 3250, 3200, 1780, 1665, 1620 cm$^{-1}$.

NMR (DMSO-d$_6$, δ): 3.55 (2H, m), 4.59 (2H, d, J=5.0 Hz), 5.06 (1H, d, J=5.0 Hz), 5.05–6.28 (3H, m), 5.80 (1H, d, J=5.0 Hz, 8 Hz), 6.44 (1H, t, J=4.0 Hz), 9.49 (1H, d, J=8.0 Hz).

(19) 7-[2-(2-Amino-5-chlorothiazol-4-yl)-2-allyloxyiminoacetamido]-3-(1,3,4-thiadiazol-2-yl)thiomethyl-3-cephem-4-carboxylic acid (syn isomer)

IR (Nujol): 3300, 3200, 1775, 1670, 1620 cm$^{-1}$.

NMR (DMSO-d$_6$, δ): 3.66 (2H, q, J=16.0 Hz), 4.41 (2H, q, J=15.0 Hz), 4.59 (2H, d, J=5.0 Hz), 5.04–5.51 (2H, m), 5.10 (1H, d, J=5.0 Hz), 5.62–6.34 (1H, m), 5.75 (1H, dd, J=5.0 Hz, 8.0 Hz), 7.30 (2H, s), 9.49 (1H, d, J=8.0 Hz), 9.50 (1H, s)

(20) 7-[2-(2-Amino-5-chlorothiazol-4-yl)-2-propargyloxyiminoacetamido]-3-cephem-4-carboxylic acid (syn isomer).

IR (Nujol): 3400, 3250, 3200, 2100, 1780, 1670, 1620 cm$^{-1}$.

NMR (DMSO-d$_6$, δ): 3.43 (1H, m), 3.52 (2H, m), 4.68 (2H, d, J=2.0 Hz), 5.04 (1H, d, J=5.0 Hz), 5.77 (1H, dd, J=5.0 Hz, 8.0 Hz), 6.43 (1H, m), 7.32 (2H, s), 9.53 (1H, d, J=8.0 Hz).

(21) 7-[2-(2-Amino-5-chlorothiazol-4-yl)-2-propargyloxyiminoacetamido]-3-(1-methyl-1H-tetrazol-5-yl)thiomethyl-3-cephem-4-carboxylic acid (syn isomer)

IR (Nujol): 3290, 3200, 2110, 1775, 1675, 1620 cm$^{-1}$.

NMR (DMSO-d$_6$, δ): 3.46 (1H, m), 3.69 (2H, m), 3.95 (3H, s), 4.32 (2H, m), 4.74 (2H, m), 5.11 (1H, d, J=5.0 Hz), 5.77 (1H, dd, J=5.0 Hz, 8.0 Hz), 7.37 (2H, broad s), 9.63 (1H, d, J=8.0 Hz).

(22) 7-[2-(2-Amino-5-chlorothiazol-4-yl)-2-propargyloxyiminoacetamido]-3-(5-methyl-1,3,4-thiadiazol-2-yl)thiomethyl-3-cephem-4-carboxylic acid (syn isomer).

IR (Nujol): 3280, 3180, 2100, 1775, 1675,, 1620 cm$^{-1}$.

NMR (DMSO-d$_6$, δ): 2.69 (3H, s), 3.47 (1H, m), 3.66 (2H, m), 4.39 (2H, q, J=13.0 Hz), 4.72 (2H, d, J=2.0 Hz), 5.32 (1H, d, J=5.0 Hz), 5.77 (1H, dd, J=5.0 Hz, 9.0 Hz), 7.38 (2H, broad s), 9.61 (1H, d, J=9.0 Hz).

(23) 7-[2-(2-Amino-5-chlorothiazol-4-yl)-2-(2-cyclopentenl-yl)oxyiminoacetamido]-3-(1,3,4-thiadiazol-2-yl)thiomethyl-3-cephem-4-carboxylic acid (syn isomer), mp. 155° to 158° C. (dec.).

IR (Nujol): 3300, 3170, 1770, 1670, 1530 cm$^{-1}$.

NMR (DMSO-d$_6$, δ): 1.83-2.50 (4H, m), 3.69 (2H, broad s), 4.45 (2H, q, J=13 Hz), 5.03-5.50 (1H, m), 5.12 (1H, d, J=5 Hz), 5.60-6.30 (3H, m), 9.50 (1H, d, J=8 Hz), 9.57 (1H, s).

(24) 7-[2-(2-amino-5-chlorothiazol-4-yl)-2-propargyloxyimino-acetamido]-3-(5-carboxymethyl-4-methyl-thiazol-2-yl)thiomethyl-3-cephem-4-carboxylic acid (syn isomer).

IR (Nujol): 3280, 3190, 1770, 1675, 1620 cm$^{-1}$.

NMR (DMSO-d$_6$, δ): 2.24 (3H, s), 3.45 (1H, m), 3.63 (2H, q, J=18.0 Hz), 3.75 (2H, s), 4.29 (2H, q, J=14.0 Hz), 4.72 (2H, d, J=2.0 Hz), 5.11 (1H, d, J=5.0 Hz), 5.78 (1H, d-d, J=5.0 Hz, 8.0 Hz), 7.38 (2H, broad s), 9.61 (1H, d, J=8.0 Hz).

(25) 7-[2-(2-amino-5-chlorothiazol-4-yl)-2-allyloxyimino acetamido]-3-(5-carboxymethyl-4-methyl-thiazol-2-yl)thiomethyl-3-cephem-4-carboxylic acid (syn isomer).

IR (Nujol): 3290, 3190, 1770, 1670, 1620 cm$^{-1}$.

NMR (DMSO-d$_6$, δ): 2.24 (3H, s), 3.63 (2H, q, J=18.0 Hz), 3.76 (2H, s), 4.30 (2H, q, J=14.0 Hz), 4.63 (2H, d, J=5.0 Hz), 5.06~5.60 (2H, m), 5.10 (1H, d, J=4.0 Hz), 5.67~6.33 (1H, m), 5.78 (1H, d, J=4.0 Hz, 8.0 Hz), 7.34 (2H, broad s), 9.54 (1H, d, J=8.0 Hz).

EXAMPLE 17

Trifluoroacetic acid (9.2 ml) was added to a suspension of 7-[2-(2-amino-5-chlorothiazol-4-yl)-2-t-butoxycarbonylmethoxyiminoacetamido]-3-methyl-3-cephem-4-carboxylic acid (syn isomer) (2.3 g) in dichloromethane (5 ml) and anisole (2.3 ml) at ambient temperature and the mixture was stirred for 1.5 hours at same temperature. To the resulting solution was added the isopropyl ether and stirred. The precipitates were collected by filtration, washed with isopropyl ether. The precipitates were added to a mixture of ethyl acetate and water, and adjusted to pH 7.5 with saturated aqueous sodium bicarbonate. The separated aqueous layer was adjusted to pH 2.2 with 10% hydrochloric acid under ice cooling. The precipitates were filtered off, washed with ice water and dried over phosphorus pentoxide in vacuo to give 7-[2-(2-amino-5-chlorothiazol-4-yl)-2-carboxymethoxyiminoacetamido]-3-methyl-3-cephem-4-carboxylic acid (syn isomer) (1.4 g).

IR (Nujol): 3400, 3300, 3200, 1775, 1730, 1630 cm$^{-1}$.

NMR (DMSO-d$_6$, δ): 2.02 (3H, s), 3.46 (2H, q, J=18.0 Hz), 4.64 (2H, s), 5.10 (1H, d, J=4.0 Hz), 5.77 (1H, d-d, J=4.0 Hz 8.0 Hz), 7.51 (2H, broad s), 9.39 (1H, d, J=8.0 Hz).

EXAMPLE 18

Trifluoroacetic acid (10 ml) was added to a solution of 7-[2-(2-amino-5-chlorothiazol-4-yl)-2-tert-butoxycarbonylmethoxyiminoacetamido]-3-(1,3,4-thiadiazol-2-yl)thiomethyl-3-cephem-4-carboxylic acid (syn isomer) (2.5 g) in methylene chloride (5.0 ml) and anisole (2.5 ml) under ice-cooling, and then the mixture was stirred for an hour at ambient temperature. The resulting solution was dropwise added to diisopropyl ether (100 ml) and then precipitates were collected by filtration. The precipitates were added to a mixture of water and ethyl acetate, and adjusted to pH 7.5 with 10% aqueous solution of sodium hydroxide. The aqueous layer was separated and adjusted to pH 2.2 with 10% aqueous hydrochloric acid to give the precipitates, which were filtered off and dried over phosphorus pentoxide in vacuo to give 7-[2-(2-amino-5-chlorothiazol-4-yl)-2-carboxymethoxyiminoacetamido]-3-(1,3,4-thiadiazol-2-yl)thiomethyl-3-cephem-4-carboxylic acid (syn isomer) (1.83 g).

IR (Nujol): 3360, 3240, 1775, 1675, 1630 cm$^{-1}$.

NMR (DMSO-d$_6$, δ): 3.69 (2H, q, J=18.0 Hz), 4.40 (2H, q, J=13.0 Hz), 4.63 (2H, s), 5.14 (1H, d, J=4.0 Hz), 5.82 (1H, dd, J=4.0 Hz, 8.0 Hz), 7.40 (2H, broad s), 9.45 (1H, d, J=8.0 Hz), 9.56 (1H, s).

EXAMPLE 19

To a mixture of anisole (2 ml) and trifluoroacetic acid (6 ml) was added 7-[2-(2-amino-5-chlorothiazol-4-yl)-2-tert-butoxycarbonylmethoxyiminoacetamido]-3-cephem-4-carboxylic acid (syn isomer) (1.7 g) at 20° to 25° C. with stirring. The reaction mixture was stirred for an hour at the same temperature. The resultant solution was poured into a mixed solvent of dissopropyl ether (300 ml) and petroleum ether (100 ml). The precipitates were collected by filtration, washed with petroleum ether, and were dissolved in an aqueous solution of sodium bicarbonate at pH 7.5. The aqueous solution was washed with ethyl acetate, adjusted to pH 2.8 with a diluted hydrochloric acid, and extracted with a mixed solvent of ethyl acetate and tetrahydrofuran. The organic layer was washed with a saturated aqueous solution of sodium chloride and dried over magnesium sulfate. After removing the solvent in vacuo, diisopropyl ether was added to the residue. The insoluble precipitates were collected by filtration to give 7-[2-(2-amino-5-chlorothiazol-4-yl)-2-carboxymethoxyiminoacetamido]-3-cephem-4-carboxylic acid (syn isomer) (1.2 g), mp 165° to 167° C. (dec.).

IR (Nujol): 3260, 1760, 1670 cm$^{-1}$.

NMR (DMSO-d$_6$, δ): 3.66 (2H, m), 4.62 (2H, broad s), 5.08 (1H, d, J=5 Hz), 5.83 (1H, dd, J=5 Hz, 9 Hz), 6.49 (1H, m), 9.50 (1H, d, J=9 Hz).

EXAMPLE 20

The following compounds were prepared according to the similar manner to that of Examples 17 to 19.

(1) 7-[2-(2-Amino-5-chlorothiazol-4-yl)-2-carboxymethoxyiminoacetamido]-2-methyl-3-cephem-4-carboxylic acid (syn isomer).

IR (Nujol): 3400, 3260, 3190, 1780, 1730, 1690, 1660, 1620 cm$^{-1}$.

NMR (DMSO-d$_6$, δ): 1.42 (3H, d, J=7.0 Hz), 3.83 (1H, m), 4.64 (2H, s), 5.12 (1H, d, J=5.0 Hz), 5.93 (1H, d-d, J=5.0 Hz, 8.0 Hz), 6.57 (1H, d, J=6.0 Hz), 7.34 (2H, broad s), 9.43 (1H, d, J=8.0 Hz).

(2) 7-[2-(2-Amino-5-chlorothiazol-4-yl)-2-carboxymethoxyiminoacetamido]-3-chloro-3-cephem-4-carboxylic acid (syn isomer)

IR (Nujol): 3400, 3270, 3200, 1780, 1720, 1685, 1655, 1620 cm$^{-1}$.

NMR (DMSO-d$_6$, δ): 3.82 (2H, q, J=18.0 Hz), 4.61 (2H, s), 5.23 (1H, d, J=4.0 Hz), 5.84 (1H, d-d, J=4.0 Hz), 7.37 (2H, broad s), 9.49 (1H, d, J=8.0 Hz).

(3) 7-[2-(2-Amino-5-chlorothiazol-4-yl)-2-carboxymethoxyiminoacetamido]-3-methoxy-3-cephem-4-carboxylic acid (syn isomer).

IR (Nujol): 3280, 3180, 1760, 1670, 1610 cm$^{-1}$.

NMR (DMSO-d$_6$, δ): 3.64 (2H, m), 3.76 (3H, s), 4.64 (2H, s), 5.15 (1H, d, J=4.0 Hz), 5.66 (1H, d-d, J=4.0 Hz, 8.0 Hz), 7.40 (2H, broad s), 9.43 (1H, d, J=8.0 Hz).

(4) 7-[2-(5-Chloro-2-trifluoroacetamidothiazol-4-yl)-2-carboxymethoxyiminoacetamido]-3-methylthiomethyl-3-cephem-4-carboxylic acid (syn isomer).

IR (Nujol): 3230, 1770, 1717, 1656 cm$^{-1}$.

(5) 7-[2-(2-Amino-5-chlorothiazol-4-yl)-2-carboxymethoxyiminoacetamido]-3-methylthiomethyl-3-cephem-4-carboxylic acid (syn isomer).

IR (Nujol): 3400, 3250, 1775, 1718, 1690, 1656 cm$^{-1}$.

(6) 7-[2-(2-Amino-5-chlorothiazol-4-yl)-2-(3-carboxy-2-propenyloxyimino)acetamido]-3-cephem-4-carboxylic acid (syn isomer).

IR (Nujol): 3200, 1775, 1660, 1630 cm$^{-1}$.

NMR (DMSO-d$_6$, δ): 3.61 (2H, broad s), 4.86 (2H, broad s), 5.12 (1H, d, J=5.0 Hz), 5.87 (1H, d-d, J=5.0 Hz, 8.0 Hz), 6.06 (1H, d, J=16.0 Hz), 6.52 (1H, m), 6.96 (1H, d-t, J=16.0 Hz 4.0 Hz), 7.79 (2H, broad s), 9.72 (1H, d, J=8.0 Hz).

(7) 7-[2-(2-Amino-5-chlorothiazol-4-yl)-2-(3-carboxy-2-propenyloxyimino)acetamido]-3-(1,3,4-thiadiazol-2-yl)thiomethyl-3-cephem-4-carboxylic acid (syn isomer).

IR (Nujol): 3300, 3200, 1770, 1670, 1630 cm$^{-1}$.

NMR (DMSO-d$_6$, δ): 3.69 (2H, m), 4.46 (2H, q, J=14.0 Hz), 4.82 (2H, m), 5.16 (1H, d, J=5.0 Hz), 5.83 (1H, d-d, J=5.0 Hz 8.0 Hz), 6.03 (1H, d, J=16.0 Hz), 6.94 (1H, d-t, J=16.0 Hz, 4.0 Hz), 7.41 (2H, broad s), 9.58 (1H, s), 9.70 (1H, d, J=8.0 Hz).

(8) 7-[2-(2-Amino-5-chlorothiazol-4-yl)-2-(1-carboxyethoxyimino)acetamido]-3-cephem-4-carboxylic acid (syn isomer).

IR (Nujol): 3250, 3190, 1775, 1665, 1620 cm$^{-1}$.

NMR (DMSO-d$_6$, δ): 1.38, 1.43 (3H, d, J=7.0 Hz), 3.60 (2H, m), 4.66 (1H, m), 5.10 (1H, d, J=5.0 Hz), 5.85 (1H, dd, J=5.0 Hz, 8.0 Hz), 6.49 (1H, m), 9.29, 9.38 (1H, d, J=8.0 Hz).

What we claim is:
1. A compound of the formula

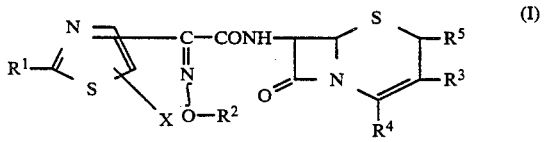

wherein
R$^1$ is amino or protected amino,
R$^2$ is carboxy(lower)alkyl, protected carboxy(lower)alkyl, carboxy(lower)alkenyl, or protected carboxy(lower)alkenyl,
R$^3$ is hydrogen, halogen, methyl, lower alkoxy, or lower alkylthiomethyl,
R$^4$ is carboxy or protected carboxy,
R$^5$ is hydrogen or lower alkyl, and
X is halogen, and pharmaceutically acceptable salts thereof.

2. The compound of claim 1, wherein
R$^1$ is amino or acylamino,
R$^2$ is carboxy(lower)alkyl, esterified carboxy(lower)alkyl, carboxy(lower)alkenyl, or esterified carboxy(lower)alkenyl,
R$^3$ is hydrogen, halogen, methyl, lower alkoxy, or lower alkylthiomethyl, and
R$^4$ is carboxy or esterified carboxy.

3. Syn isomer of the compound of claim 2.

4. The compound of claim 3, wherein
R$^1$ is amino,
R$^3$ is hydrogen,
R$^5$ is hydrogen,
R$^2$ is carboxy(lower)alkyl, lower alkoxycarbonyl(lower)alkyl, carboxy(lower)alkenyl or, lower alkoxycarbonyl(lower)alkenyl, and
R$^4$ is carboxy.

5. The compound of claim 4, which is 7-[2-(2-amino-5-chlorothiazol-4-yl)-2-(3-carboxy-2-propenyloxyimino)acetamido]-3-cephem-4-carboxylic acid (syn isomer).

6. The compound of claim 4, which is 7-[2-(2-amino-5-chlorothiazol-4-yl)-2-carboxymethoxyiminoacetamido]-3-cephem-4-carboxylic acid (syn isomer).

7. The compound of claim 4, which is 7-[2-(2-amino-5-chlorothiazol-4-yl)-2-(1-carboxyethoxyimino)acetamido]-3-cephem-4-carboxylic acid (syn isomer).

8. The compound of claim 3, wherein
R$^1$ is amino,
R$^3$ is halogen, methyl, lower alkoxy or lower alkylthiomethyl,
R$^5$ is hydrogen,
R$^2$ is carboxy(lower)alkyl or lower alkoxycarbonyl(lower)alkyl, and
R$^4$ is carboxy.

9. The compound of claim 8, which is 7-[2-(2-amino-5-chlorothiazol-4-yl)-2-carboxymethoxyiminoacetamido]-3-chloro-3-cephem-4-carboxylic acid (syn isomer).

10. The compound of claim 3, wherein
R$^1$ is amino,
R$^3$ is hydrogen,
R$^5$ is lower alkyl,
R$^2$ is carboxy(lower)alkyl or lower alkoxycarbonyl(lower)alkyl, and
R$^4$ is carboxy.

11. The compound of claim 10, which is 7-[2-(2-amino-5-chlorothiazol-4-yl)-2-carboxymethoxyiminoacetamido]-2-methyl-3-cephem-4-carboxylic acid (syn isomer).

12. A pharmaceutical antimicrobial composition comprising an effective amount of a compound of claim 1 or a pharmaceutically acceptable salt thereof in association with a pharmaceutically acceptable, substantially non-toxic carrier or excipient.

* * * * *